US011448648B2

(12) United States Patent
Beckmann et al.

(10) Patent No.: US 11,448,648 B2
(45) Date of Patent: Sep. 20, 2022

(54) COMPOSITIONS AND METHODS FOR DIAGNOSING AND DIFFERENTIATING SYSTEMIC JUVENILE IDIOPATHIC ARTHRITIS AND KAWASAKI DISEASE

(71) Applicant: Ascendant Diagnostics, LLC, Springdale, AR (US)

(72) Inventors: Patricia Beckmann, Hansville, WA (US); Lindsay Rutherford, Fayetteville, AR (US); Anna Daily, Fayetteville, AR (US); Omid Moghadam, Fayetteville, AR (US); Elizabeth Mellins, Stanford, CA (US)

(73) Assignee: ASCENDANT DIAGNOSTICS, LLC, Springdale, AR (US)

( * ) Notice: Subject to any disclaimer, the term of this patent is extended or adjusted under 35 U.S.C. 154(b) by 358 days.

(21) Appl. No.: 16/349,233

(22) PCT Filed: Nov. 10, 2017

(86) PCT No.: PCT/US2017/061057
§ 371 (c)(1),
(2) Date: May 10, 2019

(87) PCT Pub. No.: WO2018/089764
PCT Pub. Date: May 17, 2018

(65) Prior Publication Data
US 2019/0293644 A1 Sep. 26, 2019

Related U.S. Application Data

(60) Provisional application No. 62/420,991, filed on Nov. 11, 2016.

(51) Int. Cl.
*G01N 33/564* (2006.01)
*G01N 33/68* (2006.01)

(52) U.S. Cl.
CPC ....... *G01N 33/564* (2013.01); *G01N 33/6893* (2013.01); *G01N 2333/4737* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 5,045,694 A | 9/1991 | Beavis et al. | |
| 5,118,937 A | 6/1992 | Hillenkamp et al. | |
| 5,565,332 A | 10/1996 | Hoogenboom et al. | |
| 5,719,060 A | 2/1998 | Hutchens et al. | |
| 5,981,180 A | 11/1999 | Chandler et al. | |
| 6,225,047 B1 | 5/2001 | Hutchens et al. | |
| 6,524,793 B1 | 2/2003 | Chandler et al. | |
| 7,445,844 B2 | 11/2008 | Chandler et al. | |
| 8,741,584 B2 * | 6/2014 | Hirsch | G01N 33/564 435/7.1 |
| 2011/0045507 A1 | 2/2011 | Hirsch | |
| 2013/0052665 A1 | 2/2013 | Ling et al. | |

FOREIGN PATENT DOCUMENTS

| | | |
|---|---|---|
| JP | 2015-505245 T2 | 2/2015 |
| WO | WO 94/13804 | 6/1994 |
| WO | WO 99/51773 | 10/1999 |
| WO | WO 00/04389 | 1/2000 |
| WO | WO 00/56934 | 9/2000 |
| WO | WO 2012/019099 A2 | 2/2012 |
| WO | WO 2013/167727 A2 | 11/2013 |

OTHER PUBLICATIONS

Freeman et al., Kawasaki Disease: Summary of the American Heart Association Guidelines, Am. Fam. Physician, 74, (2006), p. 1141-1148 (Year: 2006).*
Putto et al., C reactive protein in the evaluation of febrile illness, Archives of Disease in Childhood, 61, (1986), p. 24-29 (Year: 1986).*
Hoovels et al., Serum calprotectin as promising diagnostic aid in predicting relapse in proteinase 3-antineutrophil cytomplasmatic antibodies-associated vasculitis, Journal of Laboratory and Precision Medicine, 2(10), (2017), (4 pages) (Year: 2017).*
Ling et al., Urine Peptidomic and Targeted Plasma Protein Analyses in the Diagnosis and Monitoring of Systemic Juvenile Idiopathic Arthritis, Clin. Proteom., 6, (2010), p. 175-193 (Year: 2010).*
Angeloni, Stephen et. al (2013) A Collection of Methods and Protocols for Developing multiplex assays with xMap Technology, Luminex xMap Cookbook, pt edition, 1-116.
Aronson, "Rare Diseases and Orphan Drugs," British Journal of Clinical Pharmacology, 2006, 61, 243-245.
Bjerre et al., "Simultaneous Detection of Porcine Cytokines by Multiplex Analysis: Development of Magnetic Bioplex Assay," Veterinary Immunology and Immunopathology, Feb. 22, 2009, 130, 53-58.
De Jager et al., "Simulataneous Detection of 15 Human Cytokines in a Single Sample of Stimulated Peripheral Blood Mononuclear Cells," Clinical and Diagnostic Laboratory Immunology, Jan. 2003, vol. 10, No. 1, pp. 133-139.
Extended European Search Report dated Apr. 16, 2020, for European Application No. 17870447.4, 8 pages.
Funding et al., "Simultaneous Quantification of 17 Immune Mediators in Aqueous Humour from Patients with Corneal Rejection," Acta Ophthalmologica Scandinavica, Dec. 2006, 84, 759-765.
International Search Report and Written Opinion dated Jan. 26, 2018, for International Application No. PCT/US2017/061057, 11 pages.
Gorelik et al., "Follistatin-like Protein 1 and Ferritin/Erythrocyte Sedimentation Rate Ratio are Potential Biomarkers for Dysregulated Gene Expression and Macrophage Activation Syndrome in Systemic Juvenile Idiopathic Arthritis," The Journal of Rheumatology, 2013, 40, 1191-1199.

(Continued)

Primary Examiner — Ellen J Marcsisin
(74) Attorney, Agent, or Firm — Cooley LLP

(57) ABSTRACT

Provided are methods, compositions, kits and the like, for diagnosing and differentiating patients with systemic juvenile idiopathic arthritis (sJIA) from patients with Kawasaki disease (KD) and other febrile illnesses.

5 Claims, 15 Drawing Sheets

(56) References Cited

OTHER PUBLICATIONS

Guo et al., "Serum calprotectin—a promising diagnostic marker for adult-onset Still's disease," Clinical Rheumatology, vol. 35, No. 1, Nov. 7, 2015, pp. 73-79.

Huang, "New Advances in Juvenile Idiopathic Arthritis," Chang Gung Med J. Jan.-Feb. 2012;35(1):1-14.

Lawson et al., "Development of an 8-plex Luminex assay to Detect Swine Cytokines for Vaccine Development: Assessment of Immunity after Porcine Reproductive and Respiratory Syndrome Virus (PRRSV) Vaccination," Vaccine, Jul. 19, 2010; vol. 28, 5356-5364.

Ling et al., "Plasma profiles in active systemic juvenile idiopathic arthritis: Biomarkers and biological implications," Proteomics, vol. 10, No. 24, Nov. 23, 2010, pp. 4415-4430.

Mottonen et al., "Comparison of Combination Therapy with Single-Drug Therapy in Early Rheumatoid Arthritis: a Randomized Trial," Lancet, May 8, 1999;353(9164):1568-73.

Pascual et al., "Role of Interleukin-1 (IL-1) in the Pathogenesis of Systemic Onset Juvenile Idiopathic Arthritis and Clinical Response to IL-1 Blockade," Journal of Experimental Medicine, vol. 201, No. 9, May 2, 2005, 1479-1486.

Pascual et al., "How the Study of Children With Rheumatic Diseases Identified Interferon-a and Interleukin-1 as Novel Therapeutic Targets," Immunological Reviews, Jun. 2008, 223, 39-59.

Ravelli et al., "Juvenile Idiopathic Arthritis," The Lancet, Mar. 3, 2007, 369, 767-778.

Reiff, "Treatment of Systemic Juevnile Idiopathic Arthritis with Tocilizulmab—the Role of Anti-Interleukin-6 Therapy after a Decade of Treatment," Biol Therapy, 2, 2012, 1-12.

Shenoi et al., "Comparison of biomarkers for systemic juvenile idiopathic arthritis," Pediatric Research, vol. 78, No. 5, Nov. 1, 2015, pp. 554-559.

Srivastava et al., "Monocytes are Resistant to Apoptosis in Systemic Juvenile Idiopathic Arthritis," Clinical Immunology, 2010, 136, 257-268.

Vastert et al., "Systemic JIA: New Developments in the Understanding of the Pathophysiology and Therapy," Best Pract Clin Rhuematol, 2009, 23, 655-664.

Woo, "Systemic juvenile idiopathic arthritis: diagnosis, management, and outcome," Nat Rev Rheumatol 2, 28-34 (2006).

Frosch,"The myeloid-related proteins 8 and 14 complex, a novel ligand of toll-like receptor 4, and interleukin-1 beta form a positive feedback mechanism in systemic-onset juvenile idiopathic arthritis," Arthritis Rheum 60(3):883-891 (2009).

Wilson, "Follistatin-like protein 1 is a mesenchyme-derived inflammatory protein and may represent a biomarker for systemic-onset juvenile rheumatoid arthritis," Arthritis Rheum 62(8):2510-2516 (2010).

* cited by examiner

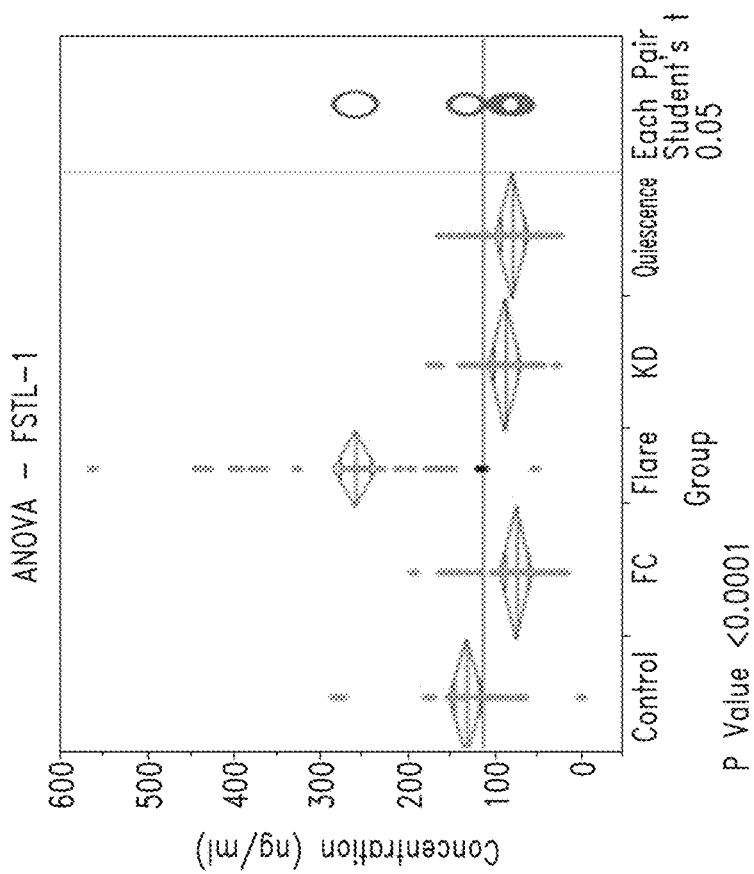
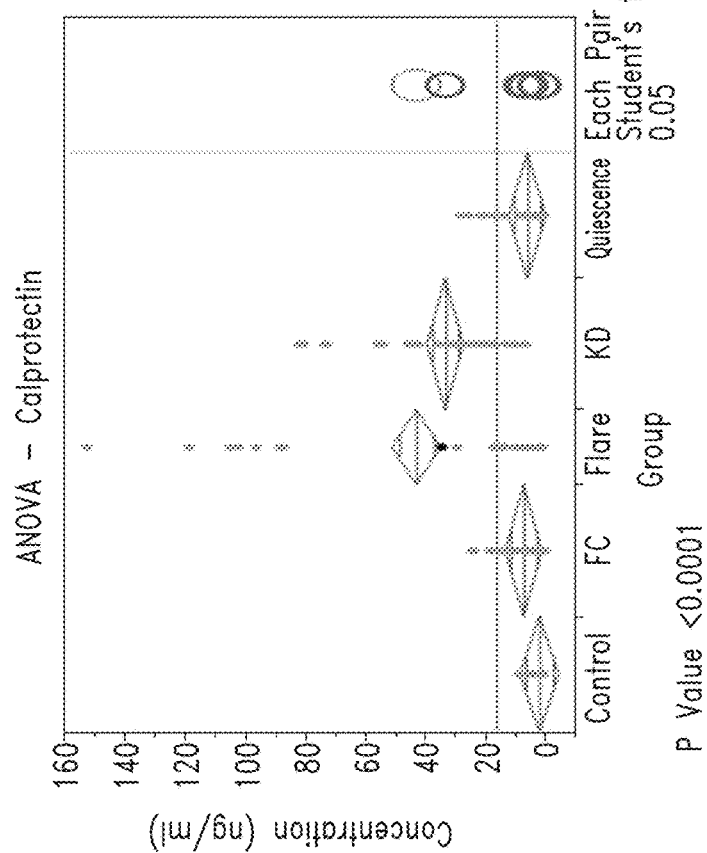
FIG. 1B
FIG. 1A

| D<br>Patient 81 Disease state | treatment intensity score | NSAID | PP PRED | MTX | Anti-TNF | IL1-RA |
|---|---|---|---|---|---|---|
| Flare (11/06) | 1 | 1 | 0 | 0 | 0 | 0 |
| Quiescence (12/06) | 5 | 1 | Score 3 | 1 | 0 | 0 |
| Quiescence (12/07) | 3 | 1 | Score 2 | 1 | 0 | 0 |
| Flare (4/07) | 3 | 1 | Score 1 | 1 | 0 | 0 |
| Flare (6/07) | 4 | 1 | Score 1 | 1 | 1 | 0 |
| Flare (12/07) | 3 | 1 | 0 | 1 | 1 | 0 |
| Quiescence (6/08) | 1 | 0 | 0 | 1 | 0 | 0 |
| Quiescence (1/09) | 0 | 0 | 0 | 0 | 0 | 0 |

COMPOSITIONS AND METHODS FOR DIAGNOSING AND DIFFERENTIATING SYSTEMIC JUVENILE IDIOPATHIC ARTHRITIS AND KAWASAKI DISEASE

CROSS-REFERENCE TO RELATED APPLICATIONS

This application is a § 371 national phase application of International Application No. PCT/US2017/061057, filed Nov. 10, 2017, which claims priority under 35 U.S.C. § 119(e) to U.S. Application No. 62/420,991, filed Nov. 11, 2016, each of which is incorporated by reference in its entirety.

BACKGROUND

Technical Field

Embodiments of the present disclosure relate to methods, compositions, kits and the like, for diagnosing and differentiating patients with systemic juvenile idiopathic arthritis (sJIA) from patients with Kawasaki disease (KD) and other febrile illnesses.

Description of the Related Art

Juvenile idiopathic arthritis (JIA) is an autoimmune disease that occurs in 1 in 1,000 children and is characterized by joint pain (arthritis) in children (2). JIA encompasses several different types of arthritis in children, including systemic juvenile idiopathic arthritis (sJIA), an orphan disease, which accounts for 10% of all JIA cases and is the most severe form due to its systemic effects (3, 4). An orphan disease is defined as a disease affecting fewer than 200,000 individuals (5). Onset of sJIA is not isolated to a specific age or gender of patients, but is often first recognized in younger children, around one or two years of age, when walking or crawling ceases due to joint pain (6). In approximately 40% of affected patients, the disease course is monocyclic with variable length of duration. However, in roughly 60% of sJIA patients, the disease manifests in polycyclic courses with periods of quiescence (inactive state of sJIA) and flare (active state of sJIA) (7).

In addition to the debilitating flares associated with sJIA, 10% of polycyclic sJIA patients will also be afflicted with macrophage activation syndrome (MAS), a severe complication of sJIA, which occurs during the active stage of the disease. MAS is caused by the release of cytokines from activated T cells and macrophages, which results in symptoms similar to sJIA flare, and which makes it difficult to differentiate between the two. MAS is one of the most serious and significant causes of mortality in children with sJIA, causing two thirds of all sJIA related deaths (8). sJIA accounts for the largest morbidity in childhood arthritis and leads to stunted growth and severe joint destruction. In addition to MAS, death occurs in 7% of patients due to active sJIA and cardiac involvement (9).

The diagnosis of sJIA is currently based on clinical findings which include joint pain, daily fever for two weeks and at least one of the following symptoms: rash, arthritis, serositisis, hepatosplenomegaly and generalized lymphadenopathy. C-reactive protein (CRP) and erythrocyte sedimentation rate (ESR) are current markers for systemic inflammation and are elevated during sJIA flare (10, 11). Timely diagnosis of sJIA can be quite difficult as symptoms can be similar to malignancy, Kawasaki Disease (KD), and other autoimmune and inflammatory diseases. Further, diagnosis is hindered in a substantial number of children, with delays greater than three months in over 25% of patients (12). Early diagnosis of sJIA reduces many long term complications and permanent disabilities caused by this disease by allowing patients to start treatment sooner.

Current treatments for sJIA can be quite costly and many of the drugs have long-lasting and in many cases detrimental side effects. In the past, systemic glucocorticoids and non-steroidal anti-inflammatory drugs (NSAIDs) were prescribed, but these drugs are often prescribed for extended time periods throughout the disease and are associated with many side effects (13). In 2011, the anti-IL-6 therapy "tocilizumab" became the first FDA approved treatment of sJIA. More recently, an interleukin-1 receptor antagonist therapy, known as "anakinra", has been approved as a treatment for sJIA (14, 15). Both of these drugs have been shown to be effective in the treatment of sJIA.

Within the pediatric rheumatology community, there is a collective consensus that an important and unmet need exists for a diagnostic test that can both diagnose sJIA and that can also differentiate sJIA from other types of fever of unknown origin (FI) illnesses, such as Kawasaki disease. Such a diagnostic test could significantly reduce medical costs currently associated with diagnosing these disorders. Currently, patients exhibiting symptoms of sJIA undergo multiple blood tests, scans and invasive procedures to determine the cause of their illness and are usually hospitalized and treated with antibiotics until all other diagnoses have been ruled out (16).

As further described herein, the present disclosure satisfies an important unmet need by providing methods, compositions, kits and the like, for diagnosing and differentiating patients with sJIA from patients with KD and other febrile illnesses. As such, the embodiments described herein advantageously offer substantially decreased time to diagnosis, and cost of diagnosis, thereby reducing patient pain and suffering and speeding access to appropriate therapy for patients afflicted with these conditions.

BRIEF SUMMARY

According to a general aspect of the present disclosure, there is provided a method for diagnosing systemic juvenile idiopathic arthritis (sJIA) in a subject, the method comprising the steps of: (i) determining the level of each of a plurality of biomarkers in a biological sample obtained from the subject, wherein the plurality of biomarkers comprises Calprotectin and Follistatin-like Protein-1 (FSTL-1); (ii) comparing the level of each of the plurality of biomarker to a corresponding predetermined diagnostic threshold value for each biomarker; and thereby providing a diagnosis of sJIA in the subject. In certain more specific embodiments, in addition to Calprotectin and FSTL-1, the plurality of biomarkers will further comprise at least one of C Reactive Protein (CRP), Serum Amyloid P (SAP) and S100A12. In still other more specific embodiments, the plurality of biomarkers will further comprise at least one of Alpha-2 Macroglobulin (A2M), Serum Amyloid A (SAA) and Apolipoprotein A1. Advantageously, the methods of the disclosure provide very high levels of diagnostic sensitivity and specificity for sJIA while evaluating the expression levels of only a small number of biomarkers. In some embodiments, for example, the plurality of biomarkers used in the methods comprises no more than 2 biomarkers, no more than 3 biomarkers, no more than 4 biomarkers or no more than 5 biomarkers.

In addition to the methods of the disclosure offering a highly effective approach for diagnosing sJIA, in certain embodiments the methods also advantageously provide a means for differentiating a diagnosis of sJIA from a diagnosis of Kawasaki Disease (KD) in the subject and/or for differentiating a diagnosis of sJIA from a diagnosis of Febrile Illness (FI) in the subject. Therefore, according to another aspect, the present disclosure provides a method for differentiating a diagnosis of systemic Juvenile Idiopathic Arthritis (sJIA), Kawasaki Disease (KD) and Febrile Illness (FI) in a subject, comprising the steps of: (i) determining the level of each of a plurality of biomarkers in a biological sample obtained from the subject, wherein the plurality of biomarkers comprises Calprotectin and Follistatin-related Protein 1 (FSTL-1); (ii) comparing the level of each of the plurality of biomarkers to a corresponding predetermined diagnostic threshold value for each biomarker; and thereby providing a diagnosis of SJIA, KD or FI in the subject. In more specific embodiments, the plurality of biomarkers further comprises at least one of C Reactive Protein (CRP), Serum Amyloid P (SAP) and S100A12. In other more specific embodiments, the plurality of biomarkers further comprises at least one of Alpha-2 Macroglobulin (A2M), Serum Amyloid A (SAA) and Apolipoprotein A1. In some embodiments of this aspect of the disclosure, the plurality of biomarkers used in the methods comprises no more than 2 biomarkers, no more than 3 biomarkers, no more than 4 biomarkers or no more than 5 biomarkers.

According to yet another general aspect of the present disclosure, there is provided a method for facilitating a determination by a medical practitioner of a need for treatment in a subject suspected of having a diagnosis of SJIA, KD or FI, comprising the steps of: (i) determining the level of each of a plurality of biomarkers in a biological sample obtained from the subject, wherein the plurality of biomarkers comprises Calprotectin and Follistatin-related Protein 1 (FSTL-1); (ii) comparing the level of each of the plurality of biomarkers to a corresponding predetermined diagnostic threshold value for each biomarker, so as to differentiate between a diagnosis of SJIA, KD and FI in the subject, thereby facilitating a determination by a medical practitioner of a need to administer to the subject a treatment for SJIA, KD or FI. In more specific embodiments, the plurality of biomarkers further comprises at least one of C Reactive Protein (CRP), Serum Amyloid P (SAP) and S100A12. In other specific embodiments, the plurality of biomarkers further comprises at least one of Alpha-2 Macroglobulin (A2M), Serum Amyloid A (SAA) and Apolipoprotein A1. Advantageously, in certain specific embodiments, the plurality of biomarkers comprises no more than 2 biomarkers, no more than 3 biomarkers, no more than 4 biomarkers or no more than 5 biomarkers. Upon making a positive diagnosis of sJIA, KD and/or FI in accordance with the methods of the disclosure, a medical practitioner is provided clarity with respect to therapeutic decisions. For example, a positive diagnosis of sJIA can facilitate a decision to administer to the subject one or more therapeutic interventions suitable for sJIA, such as agents selected from the group consisting of nonsteroidal anti-inflammatory drugs (NSAIDs), disease-modifying anti-rheumatic drugs (DMARDs), biologic agents, and intra-articular and oral steroids. In contrast, a positive diagnosis of KD by the methods of the disclosure can facilitate therapeutic decisions by a medical practitioner to administer to the subject one or more therapeutic interventions suitable for KD, which as the administration of intravenous immunoglobulin (IVIG).

In general, according to any of the methods of the disclosure, the step of determining the level of a biomarker in the biological sample (e.g., a blood sample, plasma sample or other type of sample) can be carried out by any of a variety of techniques known and available in the art. In certain particular embodiments, for example, the step of determining the level of each biomarker comprises performing an assay selected from the group consisting of an enzyme-linked immunosorbent assay (ELISA), a radioimmunoassay (RIA), an immunofluorescent assay (IFA), a sandwich assay, a magnetic capture assay, a microsphere capture assay, a Western Blot assay, surface enhanced Raman spectroscopy (SERS), flow cytometry and mass spectrometry.

According to still another general aspect, the present disclosure provides diagnostic kits suitable for diagnosing or differentiating sJIA, KD and/or FI in a subject, where the kit comprises, for example, agents (such as binding agents) effective for determining the levels of a plurality of biomarkers in a biological sample obtained from a subject. In certain specific embodiments, the kit will include agents for determining the levels of at least Calprotectin and Follistatin-related Protein 1 (FSTL-1). In other specific embodiments, the kit can further comprise agents for determining the levels of at least one of C Reactive Protein (CRP), Serum Amyloid P (SAP) and S100A12. In still other specific embodiments, the kit will further comprise agents for determining the levels of at least one of Alpha-2 Macroglobulin (A2M), Serum Amyloid A (SAA) and Apolipoprotein A1. In many embodiments, the agents effective for determining the levels of the biomarkers under evaluation are antibodies, binding fragments thereof and/or other suitable binding agents that are specific for the biomarkers under evaluation and effective for quantitating their levels. For example, in some embodiments, the kits of the disclosure will comprise a lateral flow device, or other equivalent device, which comprises antibodies or antigen-binding fragments thereof that are specific for the plurality of biomarkers being tested.

Still another general aspect of the disclosure provides a method for monitoring the progression of SJIA in a subject so as to facilitate a determination by a medical practitioner of a need for treatment, comprising the steps of (i) obtaining a biological sample from the subject; (ii) determining in the biological sample the level of each of a plurality of biomarkers, wherein the plurality of biomarkers comprises at least S100A12, CRP and Calprotectin; and (iii) comparing the level of each of the plurality of biomarkers to a corresponding predetermined diagnostic threshold value, and thereby monitoring SJIA in the subject. It has been advantageously found, for example, that elevated levels of S100A12, CRP and Calprotectin in a subject relative to their predetermined diagnostic threshold values are predictive of the progression from a quiescent SJIA stage to an active SJIA flare stage.

BRIEF DESCRIPTION OF THE DRAWINGS

FIGS. 1A-1H show Analysis of Variance (ANOVA) data for eight biomarkers which show a statistically significant difference (p-value <0.05) of means among the groups.

DETAILED DESCRIPTION

Figures 1C, 1D:
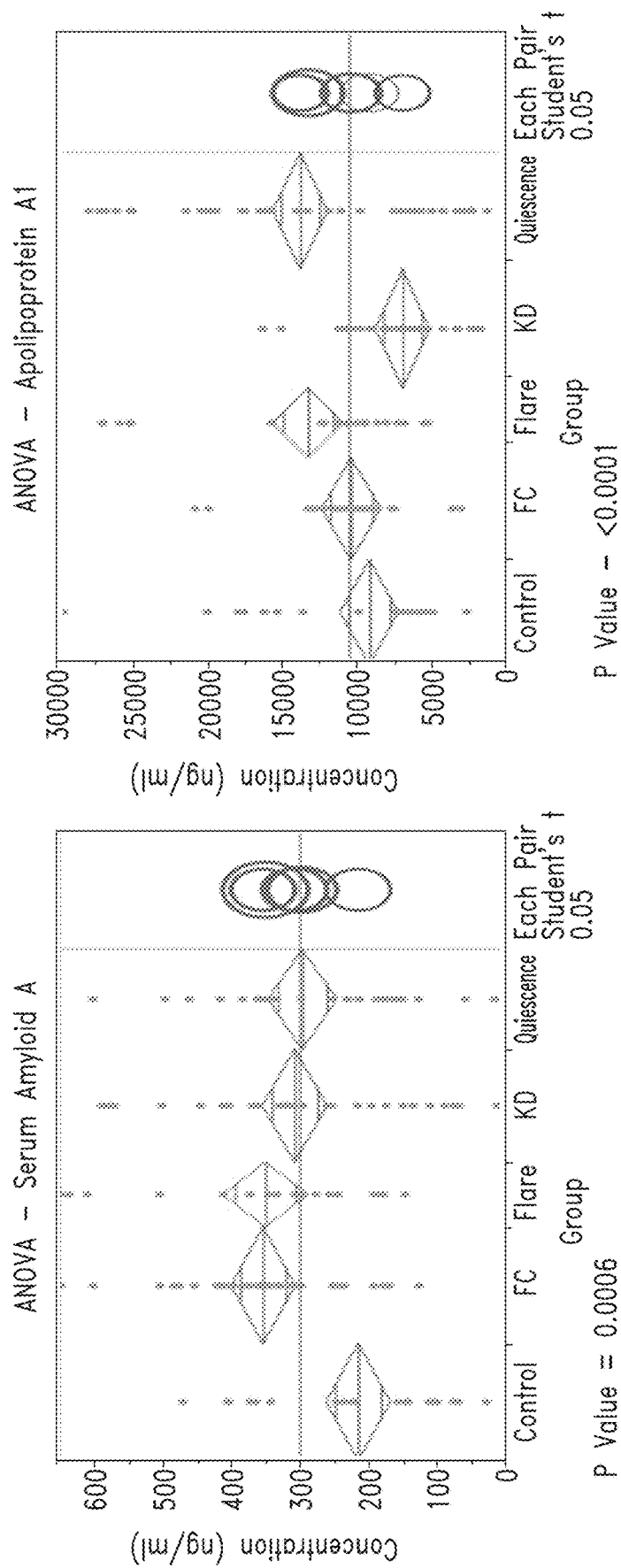

As further described herein, the present disclosure relates generally to compositions and methods for diagnosing and differentiating systemic juvenile idiopathic arthritis (sJIA), Kawasaki disease (KD) and febrile illness (FI) in a subject. Typically, the methods include determining the levels of specific biomarkers in a biological sample obtained from a subject, comparing those levels to corresponding predetermined diagnostic threshold values for each biomarker, and thereby differentiating between a diagnosis of SJIA, KD and/or FI in the subject on the basis of that comparison. The biomarkers and methods described herein thus form the basis for a simple, rapid, reliable and cost-effective means for diagnosing and differentiating between three otherwise difficult to distinguish conditions.

The practice of the present disclosure will employ, unless otherwise indicated, conventional methods of pharmacology, chemistry, biochemistry, recombinant DNA techniques and immunology, within the skill of the art. Such techniques are explained fully in the literature. See, e.g., Handbook of Experimental Immunology, Vols. I-IV (D. M. Weir and C. C. Blackwell eds., Blackwell Scientific Publications); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.).

All publications, patents and patent applications cited herein, whether supra or infra, are hereby incorporated by reference in their entireties.

As used in this specification and the appended claims, the singular forms "a", "an" and "the" include plural referents unless the content clearly dictates otherwise.

The term "about", particularly in reference to a given quantity, is meant to encompass deviations of plus or minus five percent.

The terms "polypeptide" and "protein" refer to a polymer of amino acid residues and are not limited to a minimum length, so long as they can be detected in a suitable biological sample from a subject. Thus, peptides, oligopeptides, dimers, multimers, and the like, are included, as well as full-length proteins and fragments thereof. The terms also include post-expression modifications of the polypeptide, for example, glycosylation, acetylation, phosphorylation, hydroxylation, oxidation, and the like.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the disclosure find use in experimental animals, in veterinary application, and in the development of animal models for disease, including, but not limited to, rodents including mice, rats, and hamsters; and primates.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents, including but not limited to, conditioned media resulting from the growth of cells and tissues in culture medium, e.g., recombinant cells, and cell components.

"Substantially purified" refers to nucleic acid molecules, proteins, antibodies or other biological components that are removed from their natural environment and are isolated or separated, by at least about 60%, 70%, 80%, 90%, 95% or 99%, or more, from other components with which they are naturally associated.

Biomarkers and Methods for Detection

The present disclosure is based on the discovery of particular biomarkers and combinations of biomarkers that can be advantageously used in the diagnosis and differentiation of sJIA, KD and/or FI. Generally speaking, the biomarkers of the disclosure comprise biological compounds, particularly proteins, which are differentially expressed in samples taken from patients having sJIA, KD and FI. More particularly, the biomarkers of the disclosure will typically exhibit differences in quantity and/or frequency in samples taken from subjects with sJIA, KD or FI, when compared to normal controls and/or when compared to one another (e.g., sJIA vs. KD vs. FI).

Biomarkers that can be used in the practice of the disclosure are further described and exemplified herein, and include, but are not limited to, alpha-2-macroglobulin (A2M), apolipoprotein A1 (APO A-I), C-reactive protein (CRP), calprotectin, serum amyloid A (SAA), serum amyloid P (SAP), S100A12, FSTL-1 and/or combinations thereof. For example, in one embodiment, a biomarker combination used according to the disclosure comprises at least FSTL-1. In another embodiment, a combination of biomarkers used according to the disclosure comprises at least Calprotectin and FSTL-1. In yet another embodiment, a combination of biomarkers used according to the disclosure comprises at least CRP, Calprotectin and FSTL-1. In still another embodiment, a combination of biomarkers used according to the disclosure comprises at least Calprotectin, FSTL-1 and SAP. In a further embodiment, a combination of biomarkers used in the context of the disclosure comprises at least CRP, Calprotectin, FSTL1, and SAP. In another embodiment, a combination of biomarkers used in the context of the disclosure comprises at least CRP, Calprotectin, FSTL-1, and S100A12. In a further embodiment, a combination of biomarkers used in the context of the disclosure comprises at least CRP, Calprotectin, FSTL-1, A2M, Apo-A1, S100A12, SAA, and SAP.

In certain embodiments, a combination of biomarkers used according to the disclosure (e.g., in the methods, kits, devices and/or other aspects of the disclosure) will comprise no more than 2, no more than 3, no more than 4 or no more than 5 biomarkers disclosed herein in order to diagnose or differentiate sJIA, KD and FI.

In general, a biomarker is differentially expressed between two samples if the amount of the polypeptide in one sample is statistically significantly different from the amount of the polypeptide in the other sample. For example, in certain embodiments, a polypeptide is differentially expressed in two samples if it is present at least about 120%, at least about 130%, at least about 150%, at least about 200%, at least about 300%, at least about 500%, at least about 700%, at least about 900%, or at least about 1000%, or more, greater than it is present in the other sample to which it is being compared, or if it is detectable in one sample and not detectable in the other.

Additionally, in general, a polypeptide is differentially expressed in two sets of samples if the frequency of detecting the polypeptide in samples of patients' suffering from sJIA, KD or FI, is statistically significantly higher or lower than in the control samples. For example, in certain embodiments, a polypeptide is differentially expressed in two sets of samples if it is detected at least about 120%, at least about 130%, at least about 150%, at least about 200%, at least about 300%, at least about 500%, at least about 700%, at least about 900%, or at least about 1000% more frequently or less frequently observed in one set of samples than the other set of samples.

The biological sample obtained from the subject to be diagnosed is, in many embodiments, blood or plasma, but it can also be essentially any sample from bodily fluids, tissue or cells that contain the expressed biomarkers. A "control" sample as used herein refers to a biological sample, such as blood, plasma, tissue, or cells that are not diseased. That is, a control sample is obtained from a normal subject (e.g. an individual known to not have SJIA, KD, FI or any condition or symptom associated with these conditions). A biological sample can be obtained from a subject by conventional techniques. For example, blood can be obtained by venipuncture. Plasma and serum can be obtained by fractionating whole blood according to known methods. Surgical techniques for obtaining solid tissue samples are also well known in the art.

Generally, a "control amount" of a biomarker can be any amount or a range of amounts which is to be compared against a test amount of a marker in order to diagnose or differentiate sJIA, KD and/or FI. For example, a control amount of a biomarker can be the amount of a biomarker in a person without SJIA, KD and/or FI. A control amount can be either in absolute amount (e.g., µg/ml) or a relative amount (e.g., relative intensity of signals).

A "test amount" of a biomarker refers to an amount of a biomarker present in a sample being tested. A test amount can be either an absolute amount (e.g., µg/ml) or a relative amount (e.g., relative intensity of signals).

A "diagnostic amount" of a biomarker refers generally to an amount (e.g., a threshold amount or range) of a biomarker in a subject's sample that is consistent with a particular diagnosis or a differential diagnosis of sJIA, KD and/or FI, either when considered alone or in conjunction with a particular combination of biomarkers. A diagnostic amount can be either an absolute amount (e.g., µg/ml) or a relative amount (e.g., relative intensity of signals).

It will be understood that the determination of suitable control and diagnostic values or ranges to be used for carrying out the methods herein can be readily determined by a skilled artisan taking into consideration the present disclosure.

It will also be understood that determining the level of expression of a biomarker in a sample can be carried out using any suitable method known and available in the art. Moreover, measurement of the expression level of a biomarker can be direct or indirect. For example, the levels of RNAs or proteins can be directly quantitated by known techniques. Alternatively, the amount of a biomarker can be determined indirectly by measuring the levels of cDNAs, amplified RNAs or DNAs, or by measuring quantities or activities of RNAs, proteins, or other molecules (e.g., metabolites) that are indicative of the expression level of a biomarker of interest.

In certain embodiments, the expression levels of biomarkers are determined by measuring levels of biomarker proteins or polypeptides or peptide fragments thereof using antibodies (or other binding agents) that specifically recognize the proteins or polypeptides or peptide fragments of interest. Such assays include, but are not limited to, immunohistochemistry (IHC), western blotting, enzyme-linked immunosorbent assay (ELISA), radioimmunoassays (RIA), "sandwich" immunoassays, fluorescent immunoassays, immunoprecipitation assays, the practices of which are well known in the art (see, e.g., Ausubel et al, eds, 1994, Current Protocols in Molecular Biology, Vol. 1, John Wiley & Sons, Inc., New York, which is incorporated by reference herein in its entirety).

If a biomarker is present in a sample, it will form an antibody-biomarker complex with an antibody that specifically binds the biomarker under suitable incubation conditions. The amount of an antibody-biomarker complex in the biological sample can thereby be determined and compared to a predetermined diagnostic threshold amount or range to determine if the levels determined are indicative of a positive or differential diagnosis.

When using antibodies to determine the level of one or more biomarkers according to the disclosure, such antibodies can be prepared using any suitable methods known in the art (See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975)). For example, a biomarker antigen can be used to immunize a mammal, such as a mouse, rat, rabbit, guinea pig, monkey, or human, to produce polyclonal antibodies. If desired, a biomarker antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to a biomarker antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., Nature 256, 495-97, 1985; Kozbor et al., J. Immunol. Methods 81, 3142, 1985; Cote et al., Proc. Natl. Acad. Sci. 80, 2026-30, 1983; Cole et al., Mol. Cell. Biol. 62, 109-20, 1984).

In addition, techniques developed for the production of "chimeric antibodies" can be used (Morrison et al., Proc. Natl. Acad. Sci. 81, 6851-55, 1984; Neuberger et al., Nature 312, 604-08, 1984; Takeda et al., Nature 314, 452-54, 1985). Chimeric antibodies can be constructed, for example as disclosed in WO 93/03151 and elsewhere. Binding proteins which are derived from immunoglobulins and which are multivalent and multi specific, such as the "diabodies" described in WO 94/13804, also can be used. Monoclonal and other antibodies also can be "humanized" if desired. Humanized antibodies can be produced using recombinant methodologies that are known and established in the art (e.g., U.S. Pat. No. 5,565,332; PLoS Medicine 4(5), 928-36, 2007).

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobulin libraries (Burton, Proc. Natl. Acad. Sci. 88, 11120-23, 1991). Single-chain antibodies also can be constructed using a DNA amplification method, such as PCR, using hybridoma cDNA as a template (Thirion et al., Eur. J. Cancer Prev. 5, 507-11, 1996). Single-chain antibodies can be mono- or bispecific, and can be bivalent or tetravalent. Construction of tetravalent, bispecific single-chain antibodies is taught, for example, in Coloma & Morrison, Nat. Biotechnol. 15, 159-63, 1997. Construction of bivalent, bispecific single-chain antibodies is taught in Mallender & Voss, J. Biol. Chem. 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., Int. J. Cancer 61, 497-501, 1995; Nicholls et al., J. Immunol. Meth. 165, 81-91, 1993).

Antibodies which specifically bind to a biomarker antigen also can be produced by inducing in vivo production in the lymphocyte population or by screening immunoglobulin libraries or panels of highly specific binding reagents as disclosed in the literature (Orlandi et al., Proc. Natl. Acad. Sci. 86, 3833 3837, 1989; Winter et al., Nature 349, 293 299, 1991).

Antibodies can be purified by methods well known in the art. For example, antibodies can be affinity purified by passage over a column to which the relevant antigen is bound. The bound antibodies can then be eluted from the column using a buffer with a high salt concentration.

An antibody that "specifically (or selectively) binds" or is "specifically (or selectively) immunoreactive with," a biomarker refers to a binding reaction that is determinative of the presence of the protein in a heterogeneous population of proteins and other biologics. Thus, under designated immunoassay conditions, an antibody (or other binding agent) generally binds to a particular protein at least two times the background and do not substantially bind in a significant amount to other proteins present in the sample. Typically a specific or selective reaction will be at least twice background signal or noise and more typically more than 10 to 100 times background.

The use of antibodies or fragments thereof for detecting the presence or for quantification of the biomarkers in a biological sample is well known and understood. Such methods generally comprise, for example, (i) contacting a biological sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc; and (ii) quantifying the antibody bound to the substrate. The method may additionally involve a preliminary step of attaching the antibody, either covalently, electrostatically, or reversibly, to a solid support, before subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158).

In certain embodiments, a biological sample may be fractionated prior to analysis in order to enrich the sample for lower abundance plasma proteins and to thereby facilitate detection of biomarkers. There are many ways to reduce the complexity of a sample based on the binding properties of the proteins in the sample, or the characteristics of the proteins in the sample.

In one embodiment, for example, a sample can be fractionated according to the size of the proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, and the like, for the detection of biomarkers.

In another embodiment, a sample can be fractionated by anion exchange chromatography. Anion exchange chromatography allows fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomarkers in a sample that are more negatively charged from other types of biomarkers. Proteins that are eluted with an eluant having a high pH are likely to be weakly negatively charged, and proteins that are eluted with an eluant having a low pH are likely to be strongly negatively charged. Thus, in addition to reducing complexity of a sample, anion exchange chromatography separates proteins according to their binding characteristics.

In still another embodiment, a sample can be fractionated by heparin chromatography. Heparin chromatography allows fractionation of the biomarkers in a sample also on the basis of affinity interaction with heparin and charge characteristics. Heparin, a sulfated mucopolysaccharide, will bind biomarkers with positively charged moieties, and a sample can be sequentially eluted with eluants having different pH's or salt concentrations. Biomarkers eluted with an eluant having a low pH are more likely to be weakly positively charged. Biomarkers eluted with an eluant having a high pH are more likely to be strongly positively charged. Thus, heparin chromatography also reduces the complexity of a sample and separates biomarkers according to their binding characteristics.

In yet another embodiment, a sample can be fractionated by isolating proteins that have a specific characteristic, e.g. glycosylation. For example, a sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

In another embodiment, a sample can be fractionated using a sequential extraction protocol. In sequential extraction, a sample is exposed to a series of adsorbents to extract different types of biomarkers from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomarkers. In this embodiment, the sample is applied to a first adsorbent on the probe, which is subsequently washed with an eluant. Biomarkers that do not bind to the first adsorbent are removed with an eluant. The biomarkers that are in the fraction can be applied to a second adsorbent on the probe, and so forth. The advantage of performing sequential extraction on a gas phase ion spectrometer probe is that biomarkers that bind to various adsorbents at every stage of the sequential extraction protocol can be analyzed directly using a gas phase ion spectrometer.

In yet another embodiment, biomarkers in a sample can be separated by high-resolution electrophoresis, e.g., one or two-dimensional gel electrophoresis. A fraction containing a biomarker can be isolated and further analyzed by gas phase ion spectrometry. Preferably, two-dimensional gel electrophoresis is used to generate a two-dimensional array of spots for the biomarkers. See, e.g., Jungblut and Thiede, Mass Spectr. Rev. 16:145-162 (1997).

Two-dimensional gel electrophoresis can be performed using methods known in the art. (See, e.g., Deutscher ed., Methods In Enzymology vol. 182). Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in the one dimensional array are further separated using a technique generally distinct from that used in the first separation step. For example, in the second dimension, biomarkers separated by isoelectric focusing are further resolved using a polyacrylamide gel by electrophoresis in the presence of sodium dodecyl sulfate (SDS-PAGE). SDS-PAGE allows further separation based on molecular mass. Typically, two-dimensional gel electrophoresis can separate chemically different biomarkers with molecular masses in the range from 1000-200,000 Da, even within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more biomarkers of the disclosure, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then, a spot on the membrane that approximately corresponds to the molecular weight of a biomarker can be analyzed by gas phase ion spectrometry. In gas phase ion spectrometry, the spots can be analyzed using any suitable techniques, such as MALDI or SELDI. Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of the biomarkers if desired.

In yet another embodiment, high performance liquid chromatography (HPLC) can be used to separate a mixture of biomarkers in a sample based on their different physical properties, such as polarity, charge and size. HPLC instruments typically consist of a reservoir, the mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more biomarkers can be collected. The fraction can then be analyzed by gas phase ion spectrometry to detect biomarkers.

Optionally, a biomarker can be modified before analysis to improve its resolution or to determine its identity. For example, the biomarkers may be subject to proteolytic digestion before analysis. Any protease can be used. Proteases, such as trypsin, that are likely to cleave the biomarkers into a discrete number of fragments are particularly useful. The fragments that result from digestion function as a fingerprint for the biomarkers, thereby enabling their detection indirectly. This is particularly useful where there are biomarkers with similar molecular masses that might be confused for the biomarker in question.

Also, proteolytic fragmentation is useful for high molecular weight biomarkers because smaller biomarkers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the biomarkers can be modified by the attachment of a tag of particular molecular weight that specifically binds to molecular biomarkers, further distinguishing them. Optionally, after detecting such modified biomarkers, the identity of the biomarkers can be further determined by matching the physical and chemical characteristics of the modified biomarkers in a protein database (e.g., SwissProt).

After preparation, biomarkers in a sample are typically captured on a substrate for detection. Traditional substrates include antibody-coated 96-well plates or nitrocellulose membranes that are subsequently probed for the presence of the proteins. Alternatively, protein-binding molecules attached to microspheres, microparticles, microbeads, beads, or other particles can be used for capture and detection of biomarkers. The protein-binding molecules may be antibodies, peptides, peptoids, aptamers, small molecule ligands or other protein-binding capture agents attached to the surface of particles. Each protein-binding molecule may comprise a "unique detectable label," which is uniquely coded such that it may be distinguished from other detectable labels attached to other protein-binding molecules to allow detection of biomarkers in multiplex assays. Examples include, but are not limited to, color-coded microspheres with known fluorescent light intensities (see e.g., microspheres with xMAP technology produced by Luminex (Austin, Tex.); microspheres containing quantum dot nanocrystals, for example, having different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, Calif.); chemiluminescent dyes, combinations of dye compounds; and beads of detectably different sizes. See, e.g., U.S. Pat. Nos. 5,981,180, 7,445,844, 6,524,793, Rusling et al. (2010) Analyst 135(10): 2496-2511; Kingsmore (2006) Nat. Rev. Drug Discov. 5(4): 310-320, Proceedings Vol. 5705 Nanobiophotonics and Biomedical Applications II, Alexander N. Cartwright; Marek Osinski, Editors, pp. 114-122; Nanobiotechnology Protocols Methods in Molecular Biology, 2005, Volume 303; herein incorporated by reference in their entireties).

As noted, capture reagents are well known and can be advantageously used in certain embodiments. A capture reagent refers generally to a molecule or group of molecules that specifically bind to a specific target molecule or group of target molecules. For example, a capture reagent can comprise two or more antibodies each antibody having specificity for a separate target molecule. Capture reagents can be any combination of organic or inorganic chemicals, or biomolecules, and all fragments, analogs, homologs, conjugates, and derivatives thereof that can specifically bind a target molecule.

The capture reagent can comprise a single molecule that can form a complex with multiple targets, for example, a multimeric fusion protein with multiple binding sites for different targets. The capture reagent can comprise multiple molecules each having specificity for a different target, thereby resulting in multiple capture reagent-target complexes. In certain embodiments, the capture reagent is comprised of proteins, such as antibodies.

The capture reagent can be directly labeled with a detectable moiety. For example, an anti-biomarker antibody can be directly conjugated to a detectable moiety and used in the inventive methods, devices, and kits. In the alternative, detection of the capture reagent-biomarker complex can be by a secondary reagent that specifically binds to the biomarker or the capture reagent-biomarker complex. The secondary reagent can be any biomolecule, and is preferably an antibody. The secondary reagent is typically labeled with a detectable moiety. In some embodiments, the capture reagent or secondary reagent is coupled to biotin, and contacted with avidin or streptavidin having a detectable moiety tag.

A detectable moiety or label used in conjunction with an antibody, capture reagent or other molecule will generally be capable of producing, either directly or indirectly, a detectable signal. Detectable moieties and labels suitable for use in the disclosure include, but are not limited to, radioisotopes, fluorescent dyes such as fluorescein, phycoerythrin, Cy-3, Cy-5, allophycoyanin, DAPI, Texas Red, rhodamine, Oregon green, Lucifer yellow, and the like, green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), beta-lactamase, chloramphenicol acetyltransferase (CAT), adenosine deaminase (ADA), aminoglycoside phosphotransferase (neo.sup.r, G418.sup.r) dihydrofolate reductase (DHFR), hygromycin-B-phosphotransferase (HPH), thymidine kinase (TK), lacZ (encoding .alpha.-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). Enzyme tags are used with their cognate substrate. The terms also include color-coded microspheres of known fluorescent light intensities (see e.g., microspheres with xMAP technology produced by Luminex (Austin, Tex.); microspheres containing quantum dot nanocrystals, for example, containing different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), and glass microparticles with digital holographic code images (see e.g., CyVera microbeads produced by Illumina (San Diego, Calif.). As with many of the standard procedures associated with the practice of the disclosure, skilled artisans will be aware of additional labels that can be used.

Any method known in the art for conjugating an antibody to the detectable moiety may be employed, including those methods described by Hunter et al., Nature, 144:945 (1962); David et al., Biochem., 13:1014 (1974); Pain et al., J. Immunol. Methods, 40:219 (1981); and Nygren, J. Histochem. and Cytochem., 30:407 (1982), and elsewhere.

In some embodiments, biochips can be used for capture and detection of proteins. Many protein biochips are described in the art. These include, for example, protein biochips produced by Packard BioScience Company (Meriden Conn.), Zyomyx (Hayward, Calif.), Phylos (Lexington, Mass.) and others. In general, protein biochips comprise a substrate having a surface. A capture reagent or adsorbent is attached to the surface of the substrate. Frequently, the surface comprises a plurality of addressable locations, each of which location has the capture reagent bound there. The capture reagent can be a biological molecule, such as a polypeptide or a nucleic acid, which captures other biomarkers in a specific manner. Alternatively, the capture reagent can be a chromatographic material, such as an anion exchange material or a hydrophilic material. Examples of such protein biochips are described in the following patents or patent applications: U.S. Pat. No. 6,225,047 (Hutchens and Yip, "Use of retentate chromatography to generate difference maps," May 1, 2001), International publication WO 99/51773 (Kuimelis and Wagner, "Addressable protein arrays," Oct. 14, 1999), International publication WO 00/04389 (Wagner et al., "Arrays of protein-capture agents and methods of use thereof," Jul. 27, 2000), International publication WO 00/56934 (Englert et al., "Continuous porous matrix arrays," Sep. 28, 2000).

In general, a sample containing the biomarkers is placed on the active surface of a biochip for a sufficient time to allow binding. Then, unbound molecules are washed from the surface using a suitable eluant. In general, the more stringent the eluant, the more tightly the proteins must be bound to be retained after the wash. The retained protein biomarkers then can be detected by any appropriate means, for example, mass spectrometry, fluorescence, surface plasmon resonance, ellipsometry or atomic force microscopy.

Mass spectrometry, and particularly SELDI mass spectrometry, is a particularly useful method for detection of the biomarkers of this disclosure. Laser desorption time-of-flight mass spectrometer can be used in some embodiments. In laser desorption mass spectrometry, a substrate or a probe comprising biomarkers is introduced into an inlet system. The biomarkers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry (MALDI-MS) can also be used for detecting the biomarkers described herein. MALDI-MS is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS, the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Biomarkers on the substrate surface can be desorbed and ionized using gas phase ion spectrometry. Any suitable gas phase ion spectrometer can be used as long as it allows biomarkers on the substrate to be resolved. Preferably, gas phase ion spectrometers allow quantitation of biomarkers. In one embodiment, a gas phase ion spectrometer is a mass spectrometer. In a typical mass spectrometer, a substrate or a probe comprising biomarkers on its surface is introduced into an inlet system of the mass spectrometer. The biomarkers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of biomarkers or other substances will typically involve detection of signal intensity. This, in turn, can reflect the quantity and character of biomarkers bound to the substrate. Any of the components of a mass spectrometer (e.g., a desorption source, a mass analyzer, a detector, etc.) can be combined with other suitable components described herein or others known in the art.

In addition to facilitating the diagnosis or differentiation of SJIA, KD and FI in a subject, the detection of biomarkers according to the present disclosure also gives rise to valuable alternative applications. For example, in some embodiments, there are provided methods for monitoring the response or responsiveness of a subject to a therapeutic treatment for sJIA, KD or FI. Furthermore, in additional embodiments, the disclosed methods and biomarkers can be used to screen and identify compounds that modulate expression of the biomarkers in vivo or in vitro.

Kits and Devices

In yet another aspect, the disclosure provides kits and devices for diagnosing or differentiating SJIA, KD and/or FI, wherein the kits contain agents necessary or desired for detecting and determining the levels of the biomarkers described herein in a biological sample obtained from a subject.

For example, the kit may include such things as one or more agents for detection of biomarkers, a container for holding a biological sample isolated from a human subject; printed instructions for reacting agents with the biological sample to detect the presence and/or determine the levels of at least one biomarker in the biological sample. The agents may be packaged in separate containers. The kit may further comprise one or more control reference samples and reagents for performing an appropriate assay, such as an immunoassay.

In some embodiments, a kit will comprise antibodies or binding fragments thereof that specifically bind to one or a plurality of biomarkers disclosed herein, such as biomarkers selected from the group consisting of alpha-2-macroglobulin (A2M), apolipoprotein A1 (APO A-I), C-reactive protein (CRP), calprotectin, serum amyloid A (SAA), serum amyloid P (SAP), S100A12 and FSTL-1. In a more specific embodiment, a kit comprises antibodies or other binding agents that are specific for Calprotectin and FSTL-1. In yet another embodiment, a kit comprises antibodies or other binding agents that are specific for CRP, Calprotectin and FSTL-1. In still another embodiment, a kit comprises antibodies or other binding agents that are specific for Calprotectin, FSTL-1 and SAP. In a further embodiment, a kit comprises antibodies or other binding agents that are specific for CRP, Calprotectin, FSTL1, and SAP. In another embodiment, a kit comprises antibodies or other binding agents that are specific for CRP, Calprotectin, FSTL-1, and S100A12. In a further embodiment, a kit comprises antibodies or other binding agents that are specific for CRP, Calprotectin, FSTL-1, A2M, Apo-A1, S100A12, SAA, and SAP.

In some embodiments, a kit will comprise components for performing an ELISA assay, including antibodies or other binding agents that are specific for the biomarkers and biomarker combinations described herein. In certain other embodiments, a kit will include a lateral flow device comprising antibodies or other binding agents that are specific for the biomarkers and biomarker combinations described herein.

In certain embodiments, a kit or device will include antibodies that are specific for no more than 2, no more than 3, no more than 4 or no more than 5 biomarkers disclosed herein, and effective for diagnosing or differentiating sJIA, KD and FI.

The kit or device can also comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit or device can also comprise a package insert containing written instructions for methods of diagnosing and differentiating sJIA, KD and FI.

Therefore, in certain embodiments, the kits and devices can be used to determine if a subject has sJIA or some other inflammatory condition arising, for example, from infectious illness, particularly acute febrile illness or Kawasaki disease, and to distinguish a diagnosis of sJIA from another juvenile idiopathic arthritis (JIA) disease subtype. In another example, the kits and devices can be used to predict incipient sJIA inflammatory flares in advance of clinical symptoms in a subject. In another example, the kits and devices can be used to monitor the effectiveness of treatment of a patient having sJIA. In a further example, the kits and devices can be used to identify compounds that modulate expression of one or more of the biomarkers in in vitro or in vivo animal models to determine the effects of treatment.

Below are examples of specific embodiments for carrying out the present disclosure. The examples are offered for illustrative purposes only, and are not intended to limit the scope of the present disclosure in any way.

EXAMPLES

Example 1

Identification of Biomarkers Effective in Differentiating sJIA and KD

Plasma samples from a total of 39 healthy control subjects, 42 KD subjects, 42 FI subjects, 42 sJIA flare subjects, and 42 sJIA quiescence subjects were tested using a five-point dilution series by protein microarray. The array design included three spots of capture antibody for each biomarker allowing data to be collected in triplicate for each sample. Each array also included a positive control and a blank control. Data was processed using GraphPad Prism version 11 and statistical analysis was carried out in JMPpro version 12 from SAS Institute Inc.

Figures 1E, 1F:
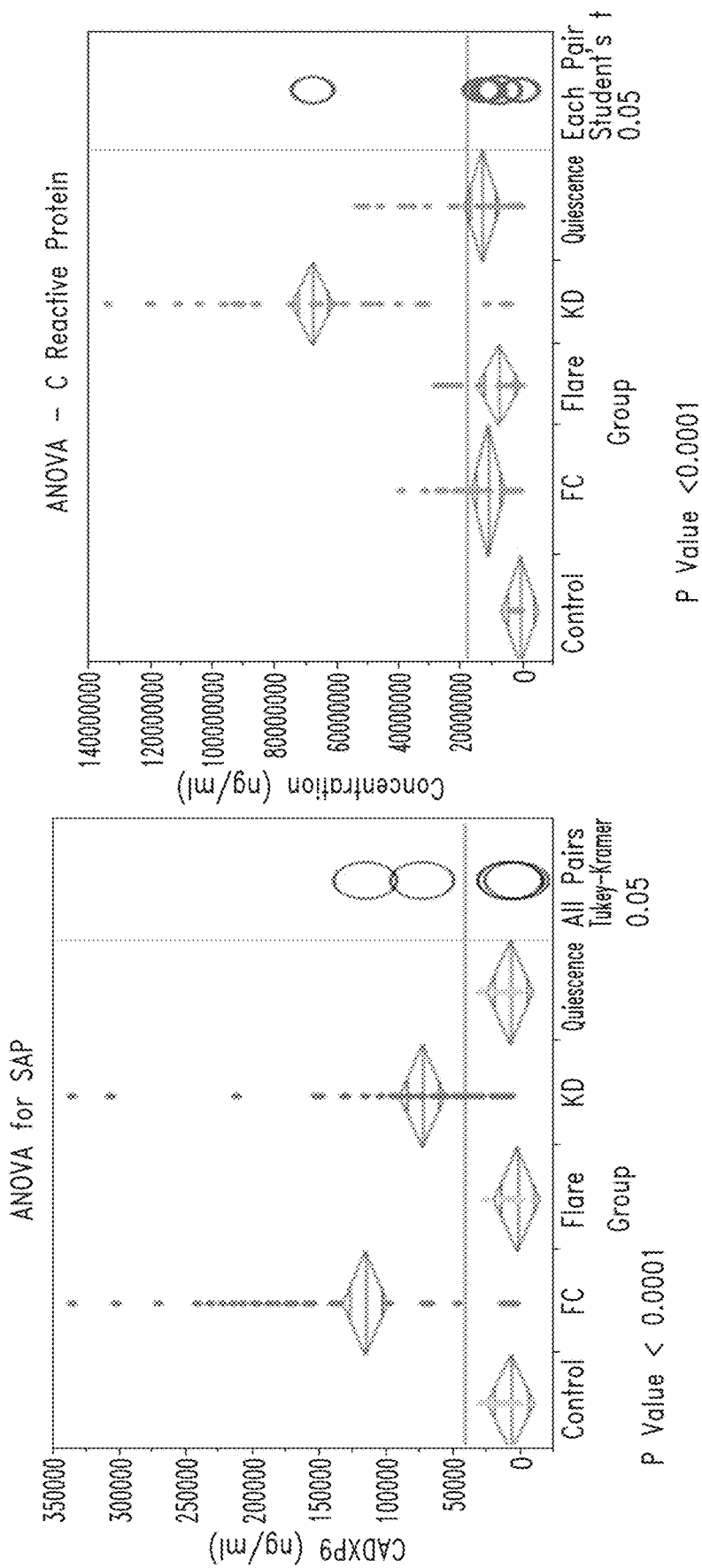
Figures 1G, 1H:
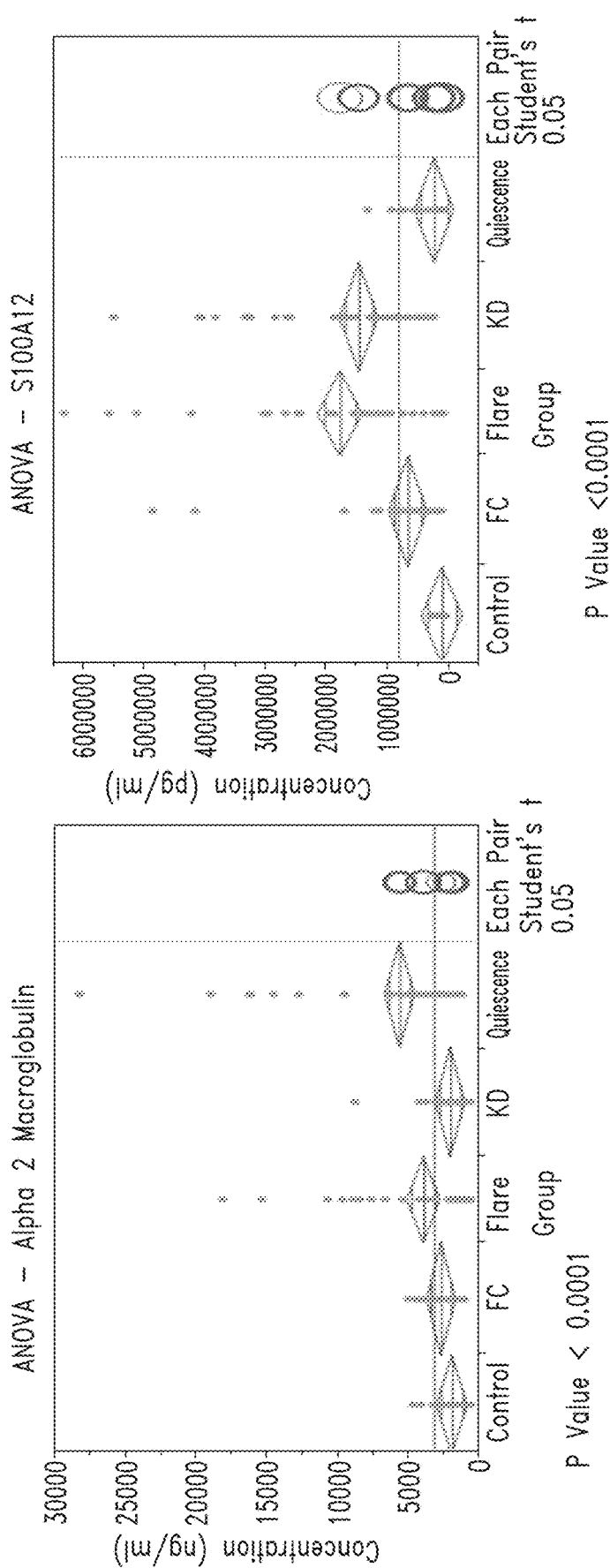
Figure 2A:
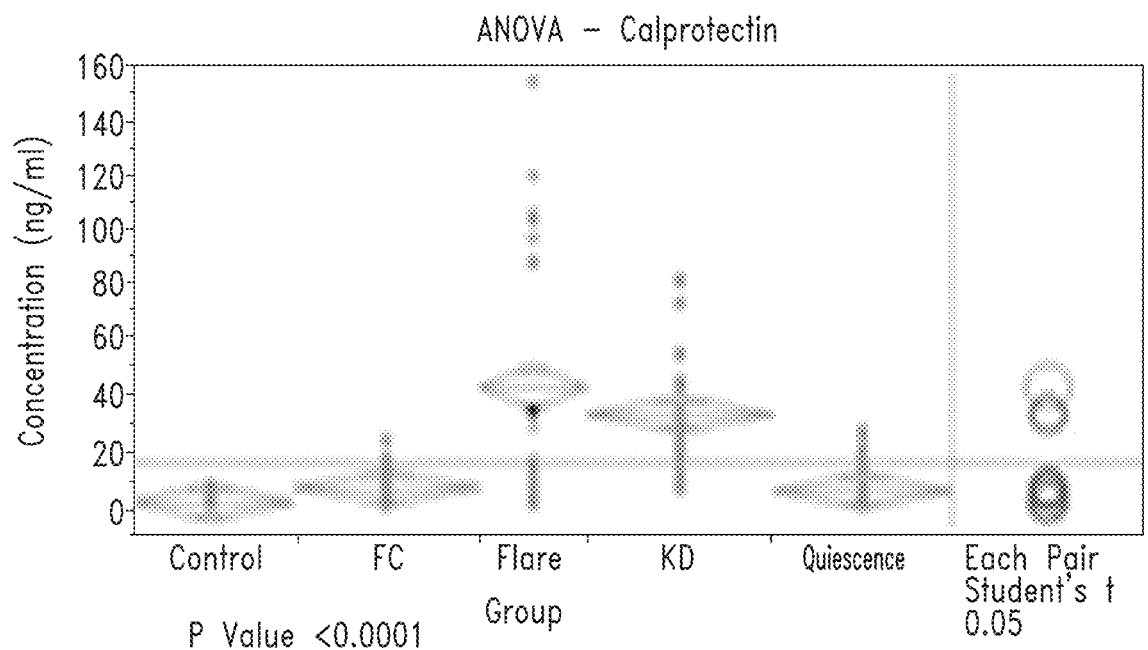
FIGS. 2A-2D show Analysis of Variance (ANOVA) data of Calprotectin (A) FSTL-1 (B) Serum Amyloid Protein (C) and C-Reactive Protein (D). Protein expression in KD and/or sJIA is upregulated compared to the other disease states (FC (febrile illness), KD, and healthy control).
Figure 2B:
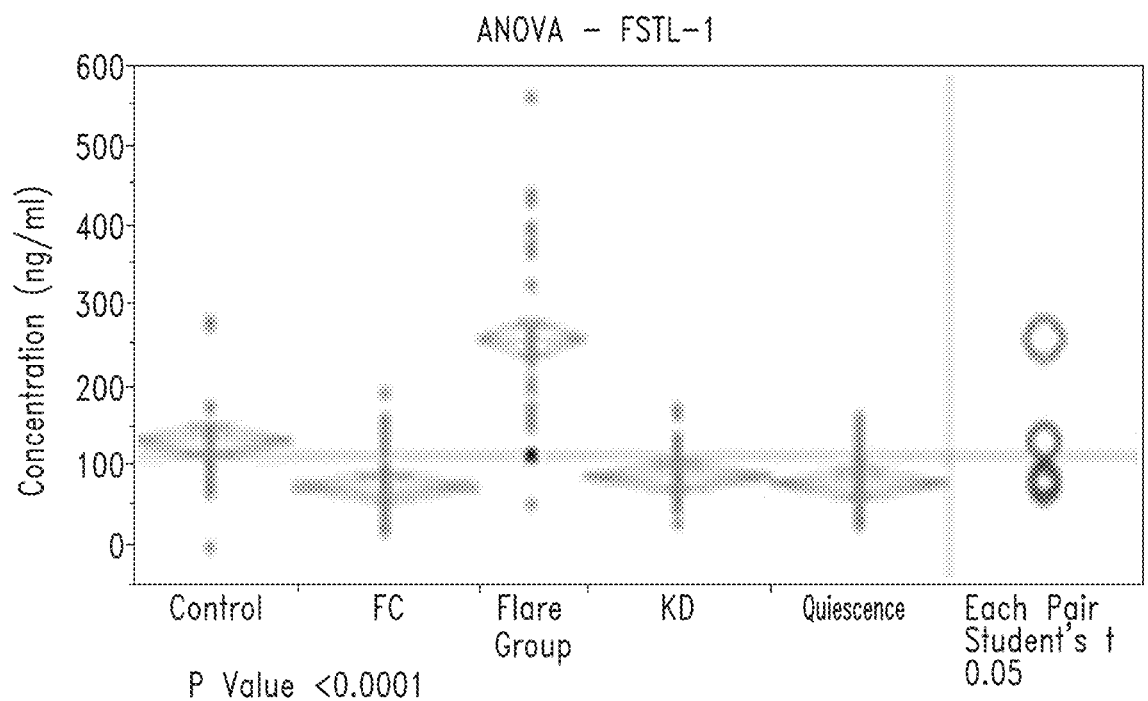
Figure 2C:
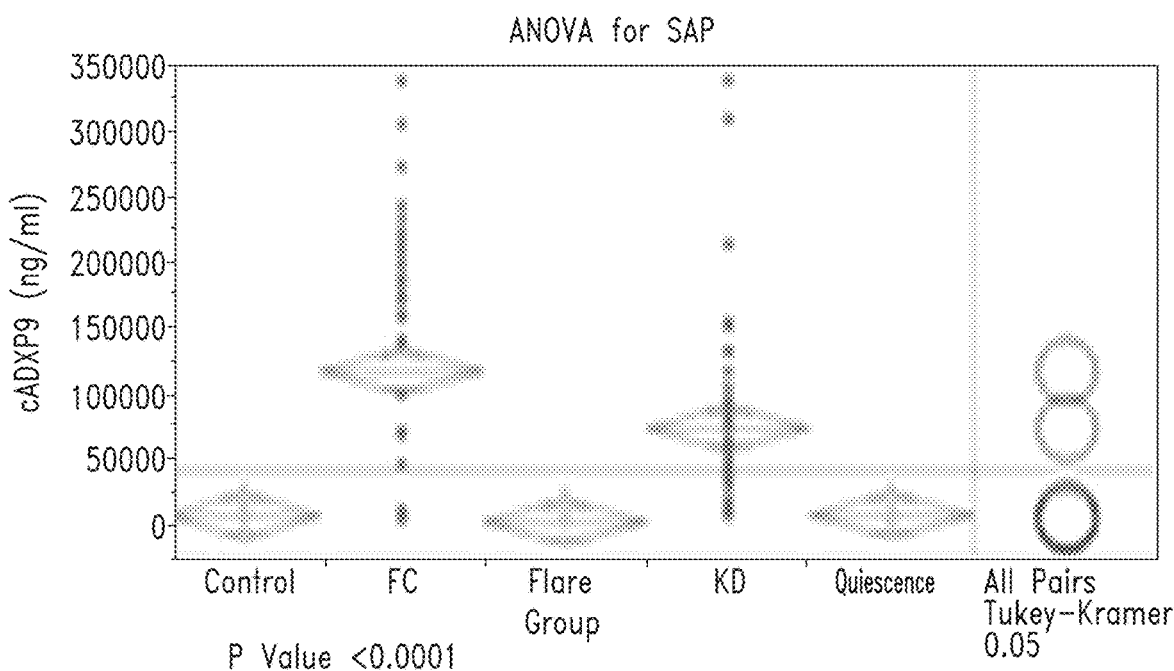
Figure 2D:
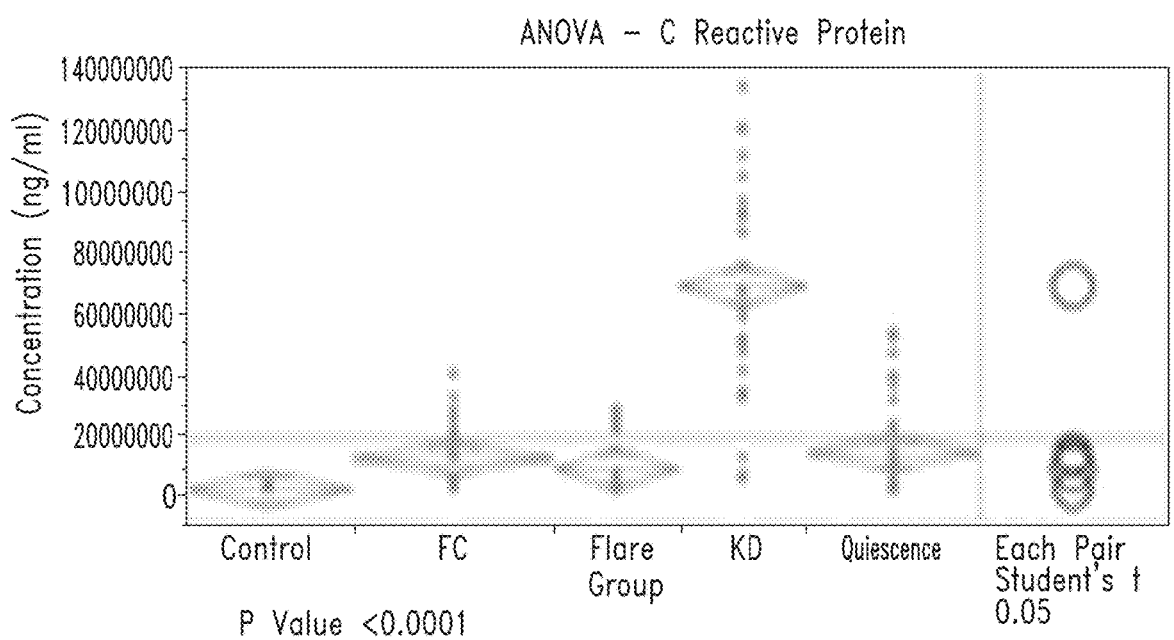
Figure 3A:
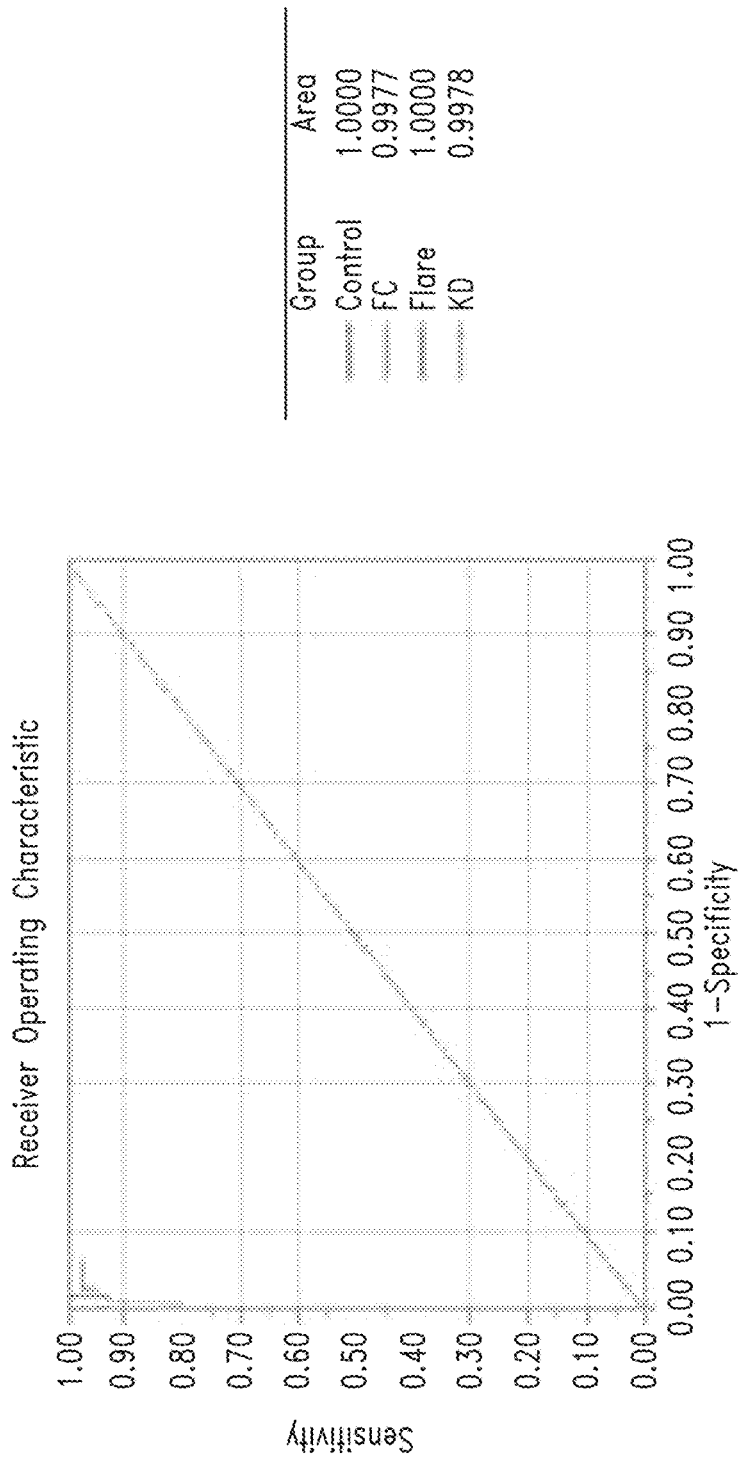
FIGS. 3A-3G show that different diagnostic panels using various combinations of proteins can be used to differentiate the four groups (Flare, KD, FC (febrile illness), and healthy control) from one another. Each combination varies in sensitivity and specificity with regard to KD, FC (febrile illness), and healthy control. However, sensitivity and specificity for sJIA Flare samples remains at 100% for all combinations evaluated. Included are an eight biomarker panel including CRP, Calprotectin, FSTL1, A2M, Apo-A1, S100A12, SAA, and SAP (A), a four biomarker panel including CRP, Calprotectin, FSTL1, and SAP (B), a three biomarker panel including CRP, Calprotectin, and FSTL1 (C), a one biomarker panel including FSTL1 (D), a two biomarker panel including Calprotectin and FSTL1 (E), a three biomarker panel including FSTL1, Calprotectin, and SAP (F), and a four biomarker panel including Calprotectin, CRP, S100A12 and FSTL1 (G).
Figure 3B:
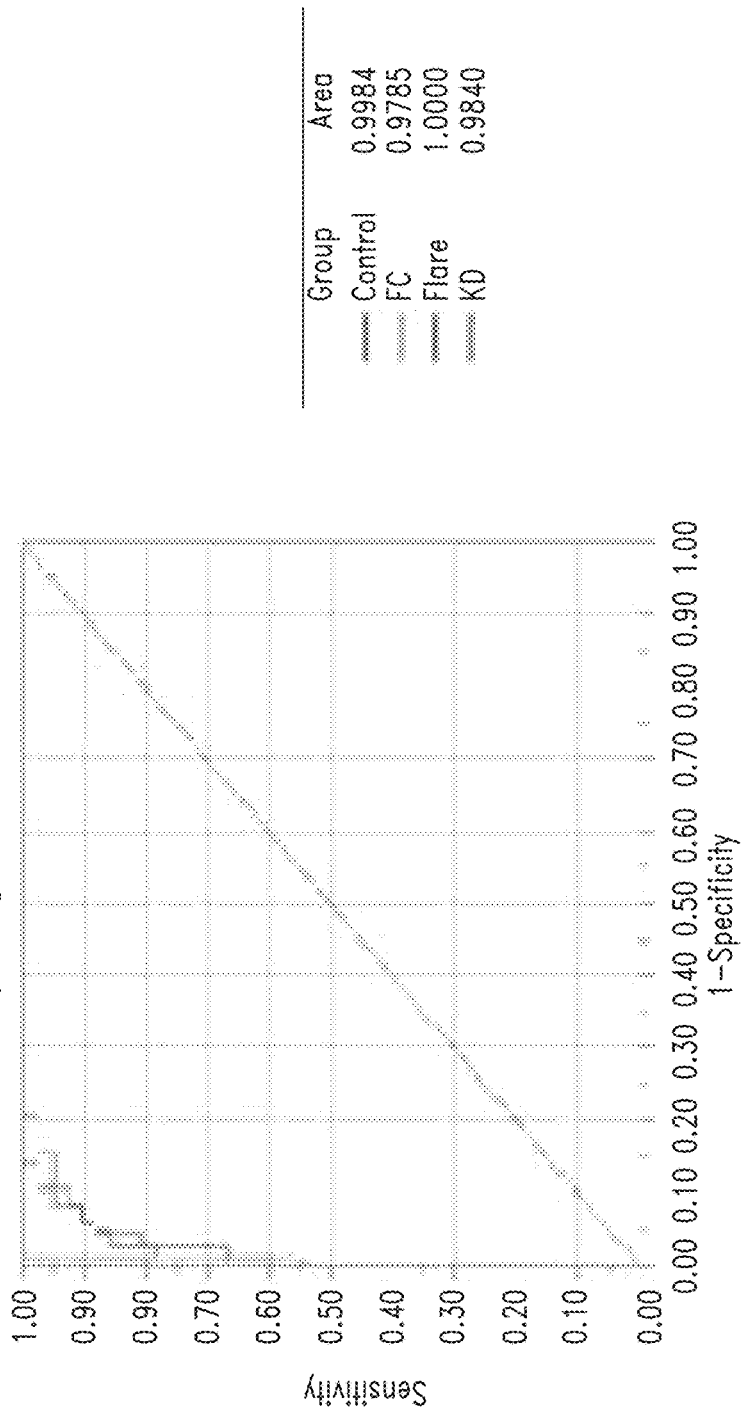
Figure 3C:
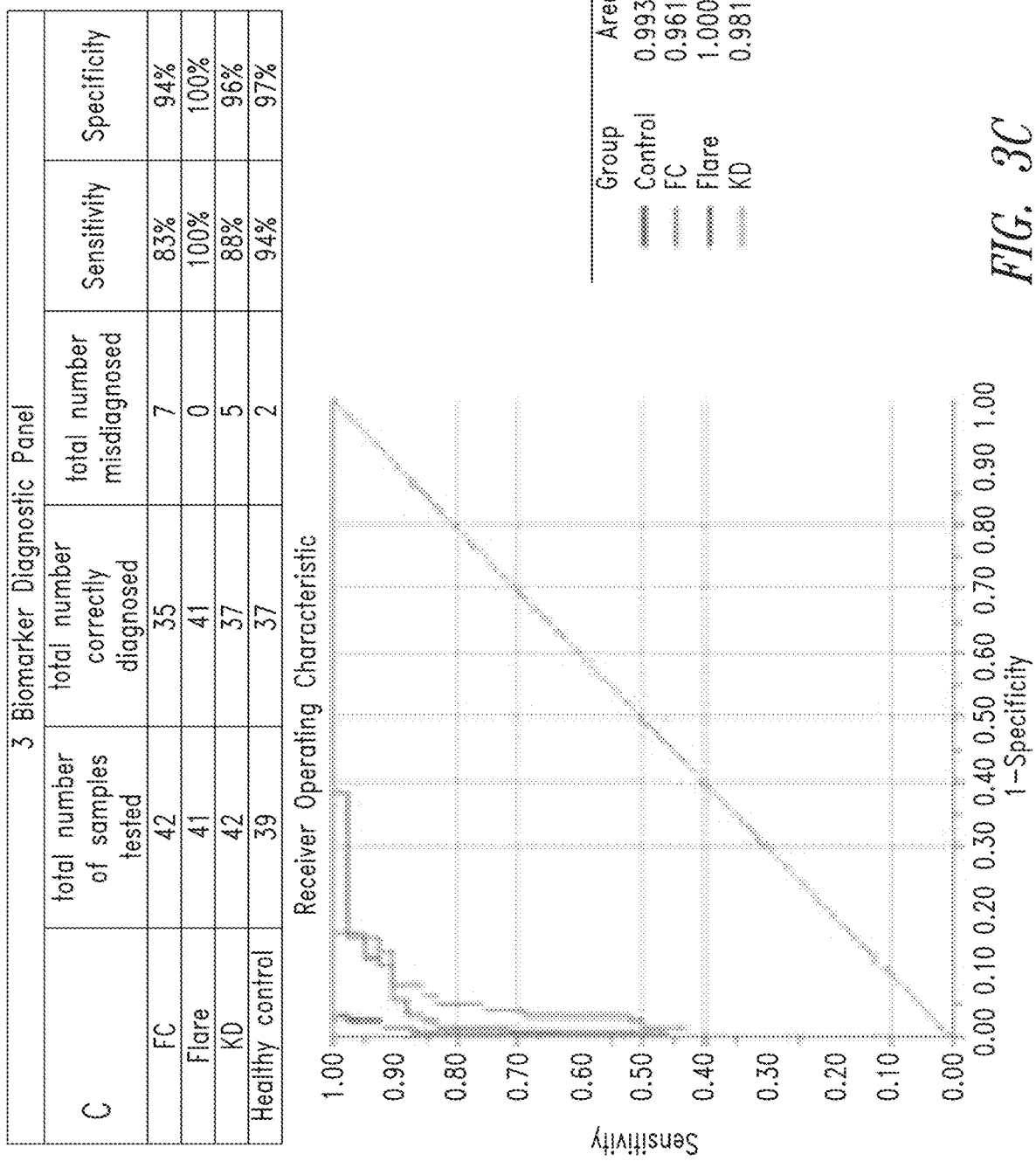
Figure 3D:
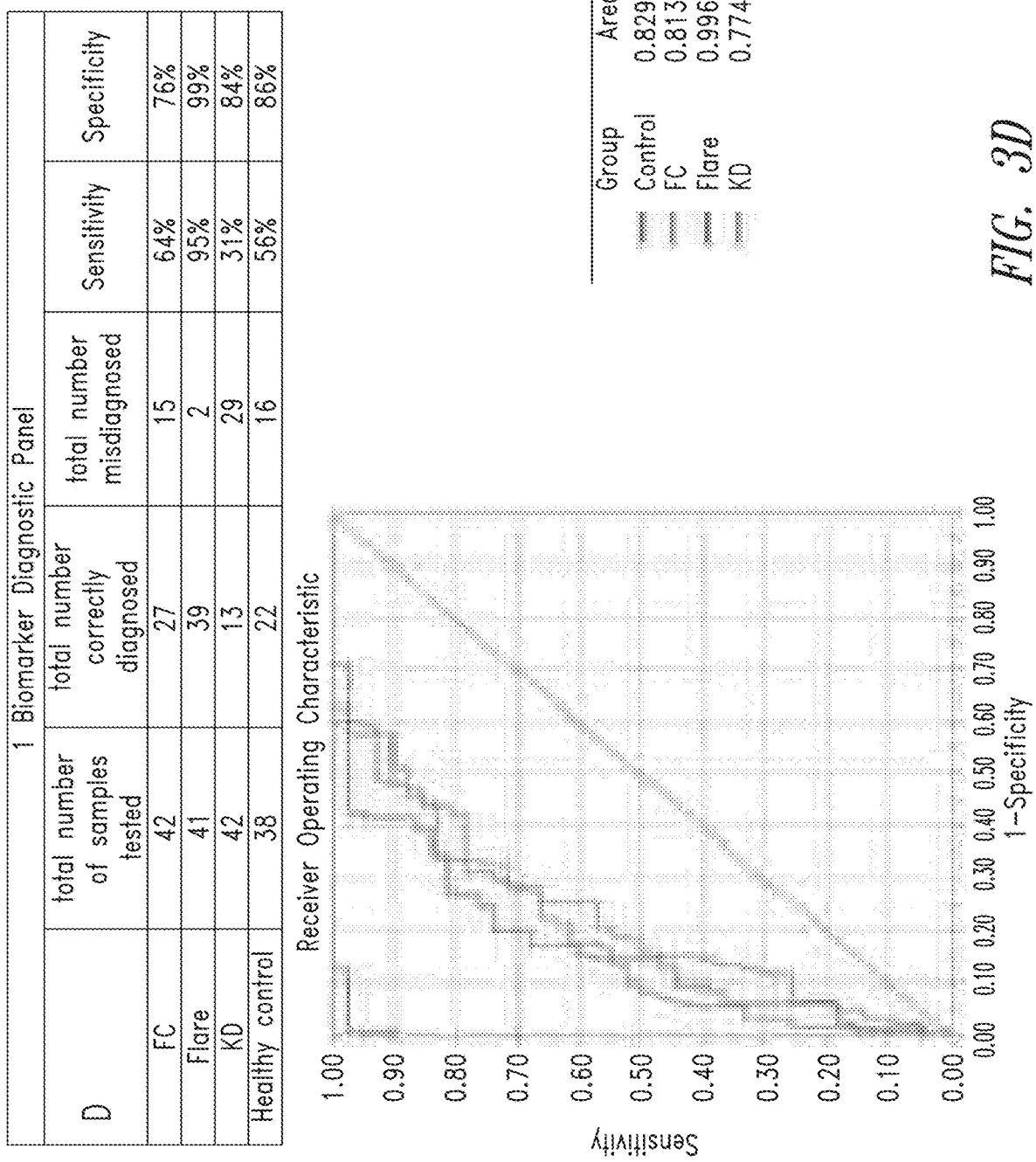
Figure 3E:
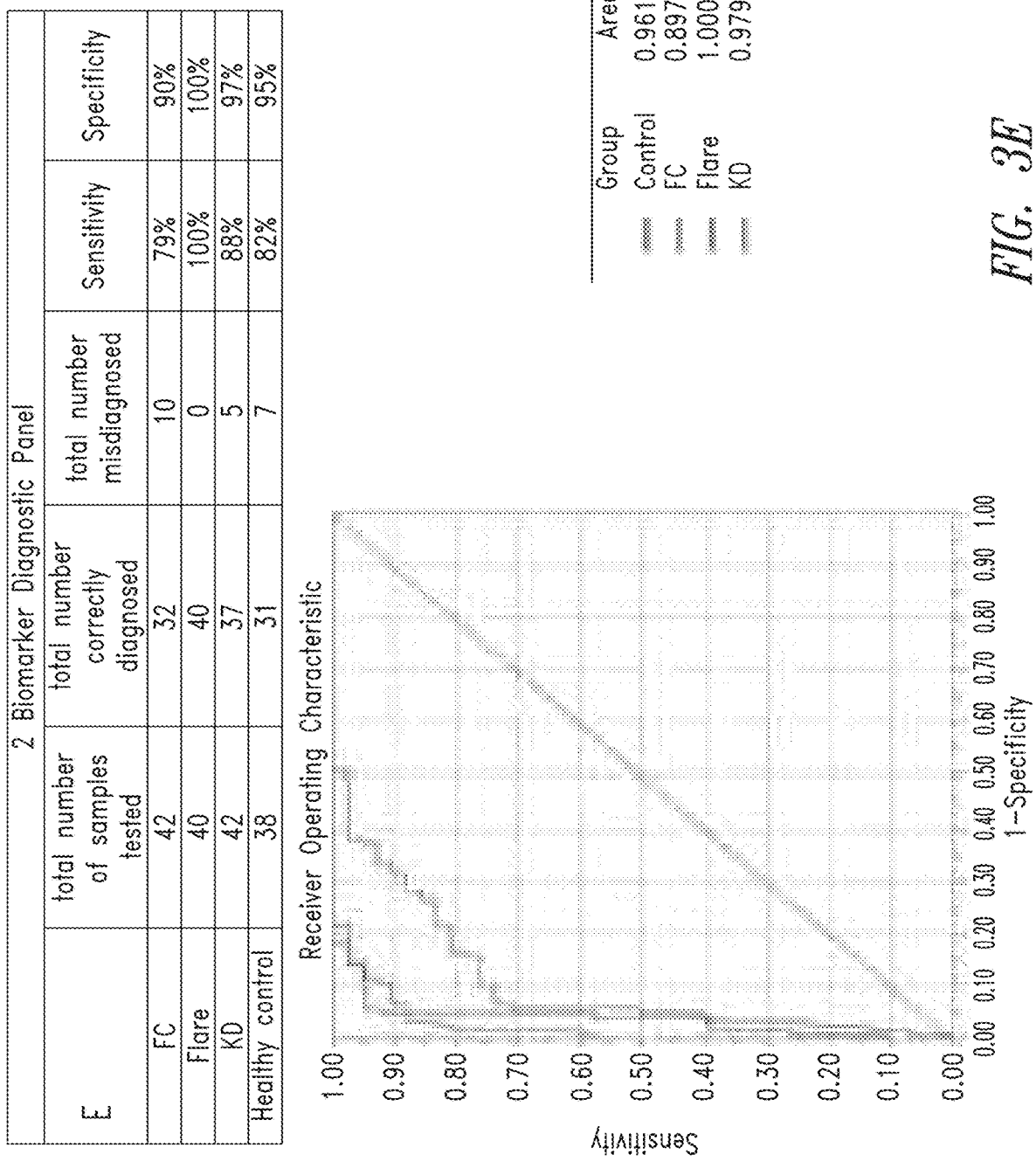
Figure 3F:
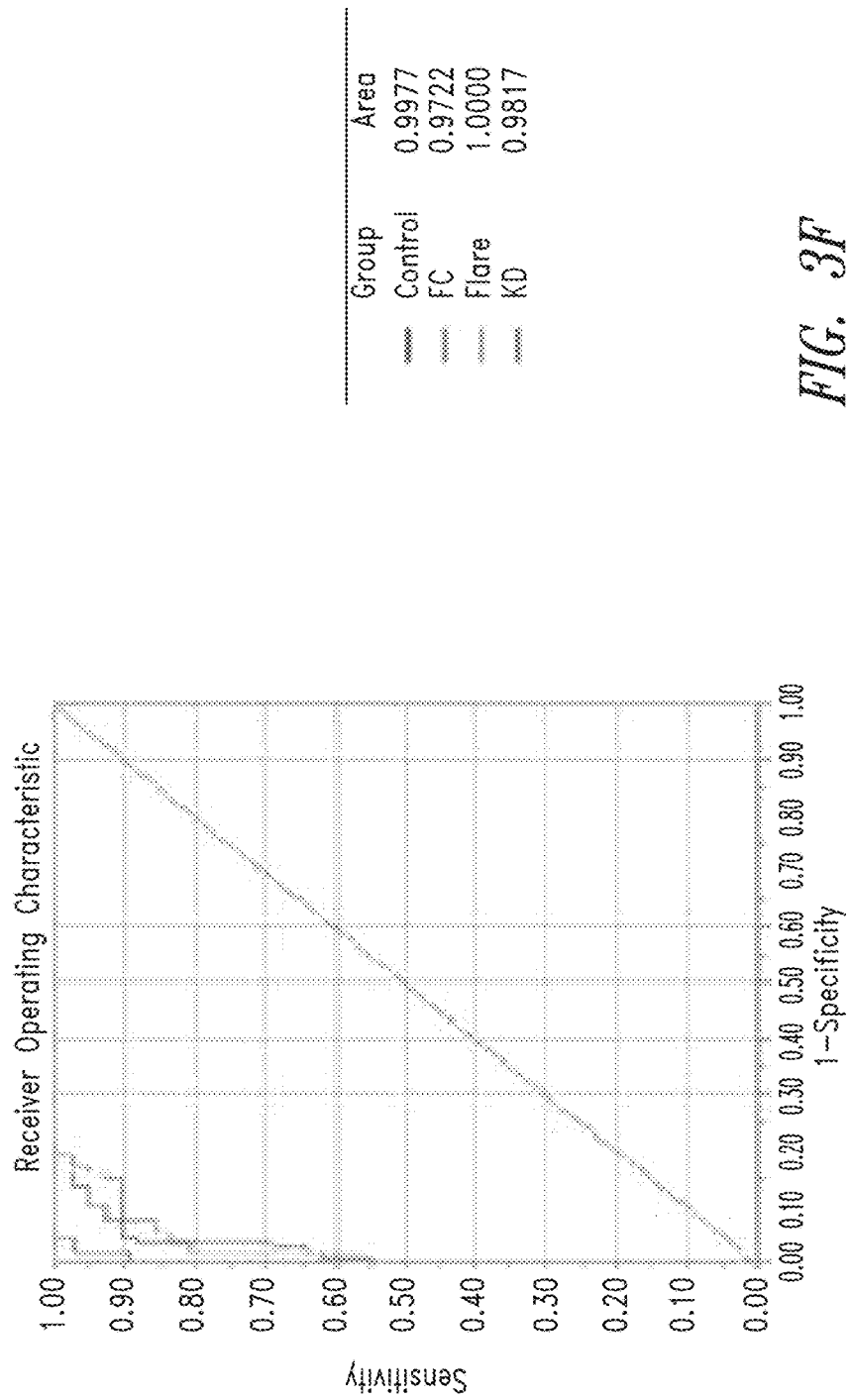
Figure 3G:
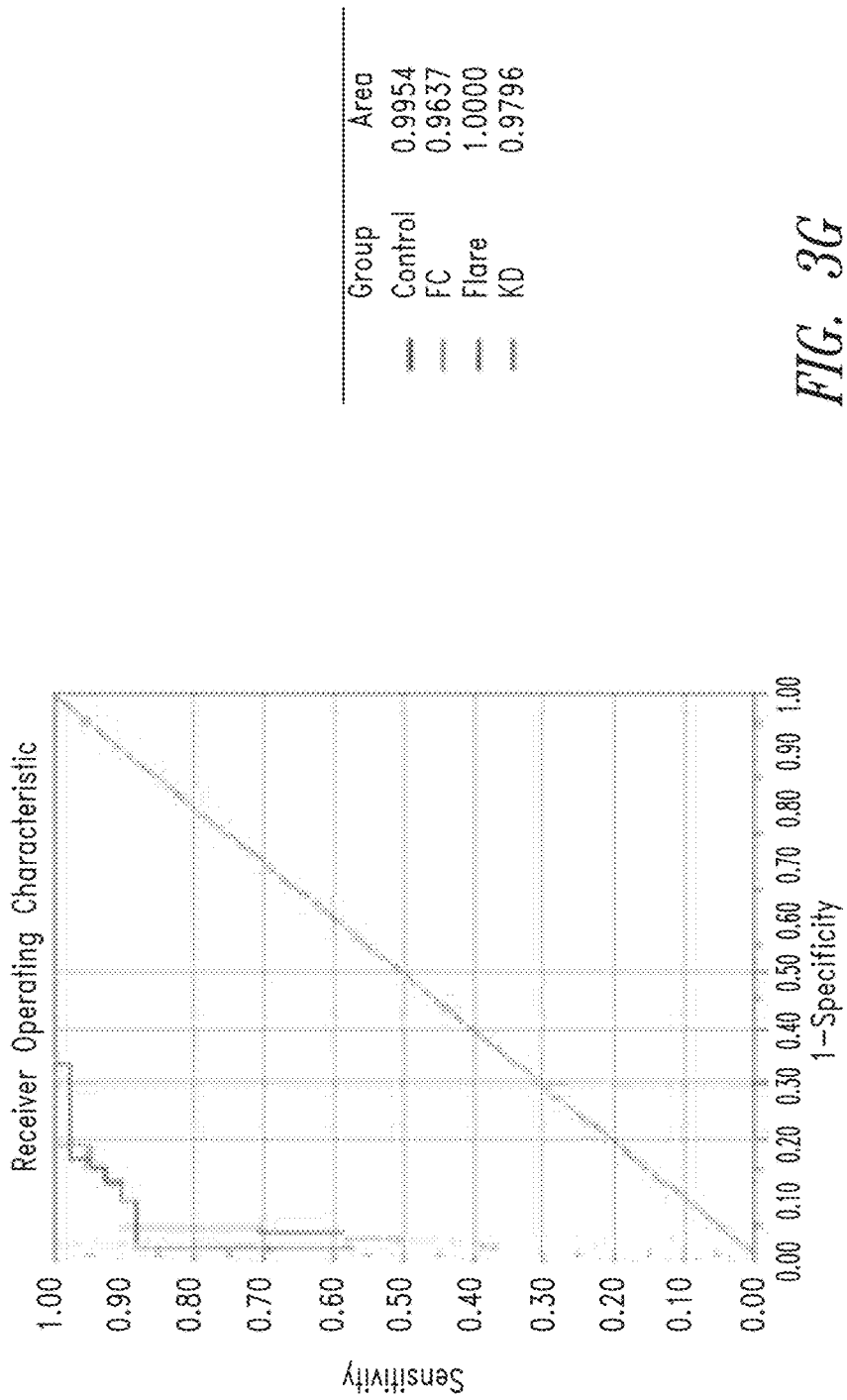

Analysis of variance (ANOVA) with student's t-test was used to analyze biomarkers for statistically significant mean differences (P-value <0.05) across these five groups. By this analysis, eight proteins had statistically significant differences among the means of one or more groups. Results from this analysis are depicted graphically in FIGS. 1 and 2. Furthermore, a nominal logistic regression analysis using these eight proteins revealed that all five groups of patients could be separated from one another with a misclassification rate of 8%. Of particular importance is the ability to clearly differentiate sJIA flare samples from all of the other groups. Using a confusion matrix generated from the nominal logistic regression, which provides the number of accurately diagnosed samples, the sensitivity and specificity of the panel for diagnosis sJIA flare samples was 100%. The healthy control group also had a sensitivity and specificity of 100%. The sensitivity and specificity for differentiating all other groups was at least 95% (FIG. 3).

In order to provide an effective and low cost assay that can provide clarity in differentially diagnosing these conditions, simplicity and ease of use are very important. Accordingly, we sought to identify the fewest number of biomarkers required to separate sJIA flare from the other groups, while still maintaining high sensitivity and specificity. Nominal logistic regression performed on the following four biomarker proteins, C Reactive Protein (CRP), Calprotectin, Follistatin-related Protein 1 (FSTL1), and Serum Amyloid P (SAP), gave rise to a sensitivity and specificity for both the sJIA flare and healthy control groups that remained at 100%. Sensitivity and specificity for the KD and FI groups was only slightly reduced to 86%, 96% and 88%, 95% respectively for the four biomarker panel. The same analysis performed on the following three biomarkers, CRP, Calprotectin and FSTL-1, also gave rise to a sensitivity and specificity for sJIA flare and healthy control groups that remained at 100%, while the sensitivity and specificity for the KD and FI groups remained above 80%. Similar analyses performed on additional biomarker combinations is shown in FIG. 3.

Example 2

Monitoring Patients and Predicting Flare Occurrence

Figure 4A:
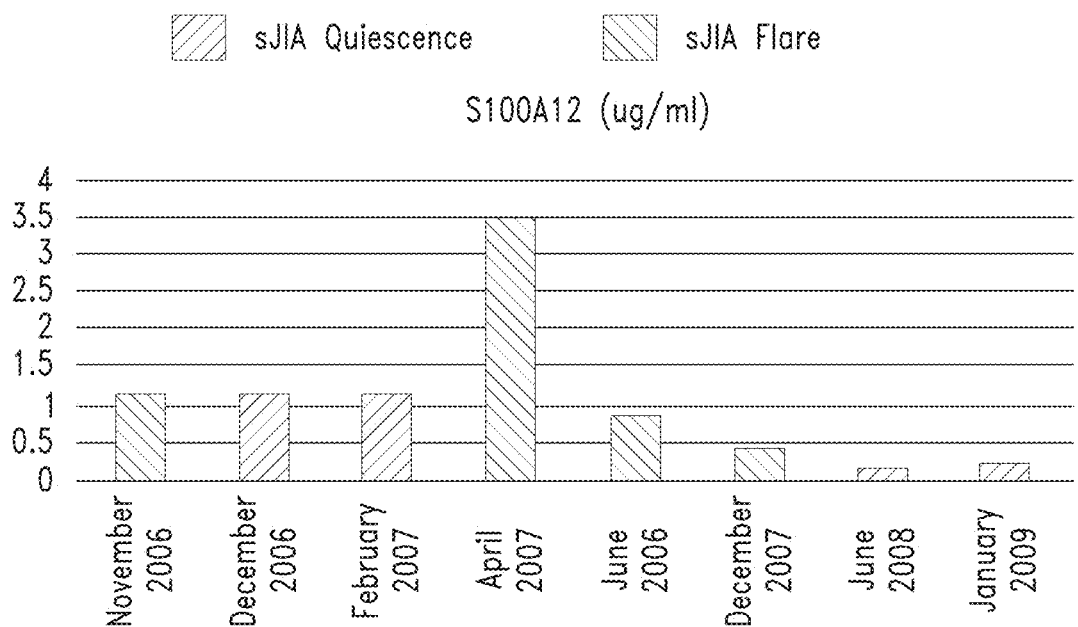
FIGS. 4A-4D show the results of a Monitoring Study in which protein expression with respect to flare "active sJIA" and quiescence "inactive sJIA" samples was evaluated. Three biomarkers evaluated show an altered expression with change in disease state (A-C) typically increasing with flare and decreasing with quiescence. It appears that protein variation could be affected by different types of therapies (D).
Figure 4B:
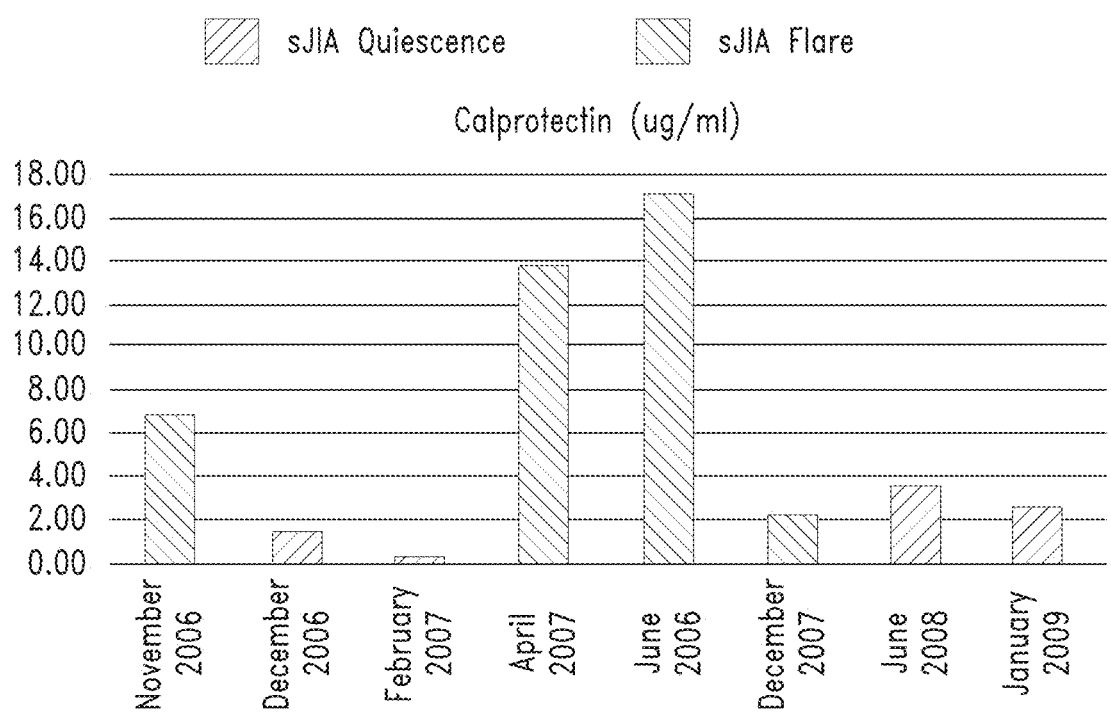
Figures 4C, 4D:
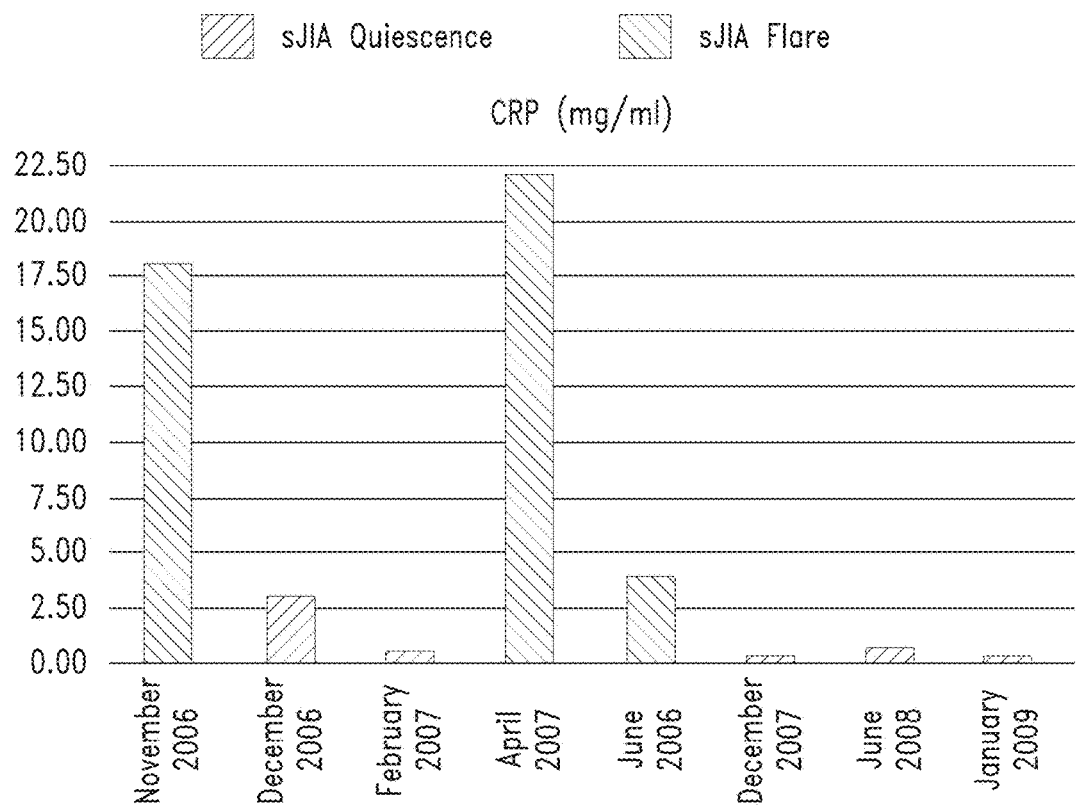

In this example, biomarkers were evaluated in patients during active (flare) and inactive (quiescent) stages of sJIA. Plasma samples analyzed were collected from the same subjects as they went through distinct cycles of flare and quiescence. Using this approach, it was found that three particular biomarkers, CRP, Calprotectin and S100A12, showed distinct expression patterns associated with changes in disease state, i.e. increasing with flares and decreasing with quiescence (FIG. 4). Accordingly, biomarkers such as these may be used, for example, in methods for monitoring subjects with sJIA and/or for predicting the onset of active flare.

REFERENCES

1. Srivastava, Shivani et. al (2010) Monocytes are Resistant to Apoptosis in Systemic Juvenile Idiopathic Arthritis. *Clinical Immunology* 136, 257-268.

2. Woo, P. (2006) Systemic Juvenile Idiopathic Arthritis: Diagnosis, Management, and Outcome. *Nature Clinical Practice Rheumatology* 2.
3. Huang, Jing-Long. (2012) New Advances in Juvenile Idiopathic Arthritis, *Chang Gung Med J* 35.
4. Pascual, V. (2005) Role of Interleukin-1 (IL-1) in the Pathogenesis of Systemic Onset Juvenile Idiopathic Arthritis and Clinical Response to IL-1 Blockade. *Journal of Experimental Medicine* 201, 1479-1486
5. Aronson, J. K. (2006) Editors' View Rare Diseases and Orphan Drugs, *British Journal of Clinical Pharmacology* 61, 243-245.
6. Reiff, A. (2012) Treatment of Systemic Juvenile Idiopathic Arthritis with Tocilizulmab—the Role of Anti-Interleukin-6 Therapy after a Decade of Treatment Biologics in Therapy, *Cancer Biology and Therapy* 2, 1-12.
7. Ling, X. B.; Park, J. L.; Carroll, T.; Nguyen, K. D.; Lau, K.; Macaubas, C.; Chen, E.; Lee, T.; Sandborg, C.; Milojevic, D.; Kanegaye, J. T.; Gao, S.; Burns, J.; Schilling, J.; Mellins, E. D. (2010) Plasma Profiles in Active Systemic Juvenile Idiopathic Arthritis: Biomarkers and Biological Implications, *PROTEOMICS* 10, 4415-4430.
8. Gorelik, Mark et. al (2013) Follistatin-like Protein 1 and Ferritin/Erythrocyte Sedimentation Rate Ratio are Potential Biomarkers for Dysregulated Gene Expression and Macrophage Activation Syndrome in Systemic Juvenile Idiopathic Arthritis. *The Journal of Rheumatology* 40, 1191-1199.
9. Ravelli, Angelo; Martini, Alberto. (2007) Juvenile Idiopathic Arthritis. *The Lancet* 36. 767-778.
10. Vastert, S. J.; Kuis, W.; Grom, A. A. (2009) Systemic JIA: New Developments in the Understanding of the Pathophysiology and Therapy. *Best Pract Clin Rheumatol* 23, 655-664.
11. Möttönen, T.; Hannonen, P.; Leirisalo-Repo, M.; Nissilä, M.; Kautiainen, H.; Korpela, M.; Laasonen, L.; Julkunen, H.; Luukkainen, R.; Vuori, K.; Paimela, L.; Blåfield, H.; Hakala, M.; Ilva, K.; Yli-Kerttula, U.; Puolakka, K.; Järvinen, P.; Hakola, M.; Piirainen, H.; Ahonen, J.; Pälvimäki, I.; Forsberg, S.; Koota, K.; Friman, C.(1999) Comparison of Combination Therapy with Single-Drug Therapy in Early Rheumatoid Arthritis: a Randomized Trial. *The Lancet* 353, 1568-1573.
12. Childhood Arthritis and Rheumatology Alliance (CARRA): Unpublished Data, 2013.
13. Pascual, Virginia; Allantaz, Florence; Patel, Pinakeen; Palucka, Karolina, A; Chaussabel, Damien; Banchereau, Jacques (2008) How the Study of Children With Rheumatic Diseases Identified Interferon-α and Interleukin-1 as Novel Therapeutic Targets. *Immunological Reviews* 223, 39-59.
14. Angeloni, Stephen et. al (2013) A Collection of Methods and Protocols for Developing multiplex assays with xMap Technology, Luminex xMap Cookbook. 1st edition, 1-116.
15. Microbead Trappind Device (2012).
16. De Jager, W.; Velthuis, H. T.; Prakken, B. J.; Kuis, W.; Rijkers, G. T. (2003) Simultaneous Detection of 15 Human Cytokines in a Single Sample of Stimulated Peripheral Blood Mononuclear Cells. *Clinical and Vaccine Immunology* 10, 133-139.
17. Lawson, S.; Lunney, J.; Zuckermann, F.; Fern; Osorio, O.; Nelson, E.; Welbon, C.; Clement, T.; Fang, Y.; Wong, S.; Kulas, K.; Christopher-Hennings, J.; Osorio, F. (2010) Development of an 8-plex Luminex assay to Detect Swine Cytokines for Vaccine Development: Assessment of Immunity after Porcine Reproductive and Respiratory Syndrome Virus (PRRSV) Vaccination. *Vaccine* 28, 5356-5364.
18. Bjerre, M.; Hansen, T. K.; Flyvbjerg, A.; Tønnesen, E. (2009) Simultaneous Detection of Porcine Cytokines by Multiplex Analysis: Development of Magnetic Bioplex Assay. *Veterinary Immunology and Immunopathology* 130, 53-58.
19. Funding, M.; Hansen, T. K.; Gjedsted, J.; Ehlers, N. (2006) Simultaneous Quantification of 17 Immune Mediators in Aqueous Humour from Patients with Corneal Rejection. *Acta Ophthalmologica Scandinavica* 84, 759-765.

Other embodiments and uses will be apparent to one skilled in the art in light of the present disclosure and the preceding examples. Further, those skilled in the art will appreciate that numerous changes and modifications can be made to the embodiments of the disclosure and that such changes and modifications can be made without departing from the disclosure. It is, therefore, intended that the appended claims cover all such equivalent variations as fall within the spirit and scope of the disclosure.

The invention claimed is:

1. A method for diagnosing and treating systemic Juvenile Idiopathic Arthritis (sJIA) flare in a subject, the method comprising the steps of:
   (i) determining the expression level of each of a plurality of biomarkers in a blood or plasma sample obtained from the subject, wherein the plurality of biomarkers comprises Calprotectin, Follistatin-related protein (FSTL-1), C Reactive Protein (CRP) and Serum Amyloid P (SAP;
   (ii) providing a diagnosis of sJIA flare in the subject if the expression level of Calprotectin is higher compared to the expression level in healthy control subjects or a subjects with febrile illness, the expression level of FSTL-1 is higher compared to the expression level in healthy control subjects, subjects with febrile illness or a subjects with Kawasaki disease, the expression level of CRP is lower compared to the expression level in subjects with Kawasaki disease, and the expression level of SAP is lower compared to the expression level in subjects with febrile illness or Kawasaki disease; and
   (iii) treating sJIA flare in the diagnosed subject with an agent selected from the group consisting of nonsteroidal anti-inflammatory drugs (NSAIDs), disease modifying anti-rheumatic drugs (DMARDs), biologic agents selected from anti-IL-6 therapy and interleukin-1 receptor antagonist therapy, and intra-articular and oral steroids.

2. The method of claim 1, where the plurality of biomarkers further comprises S100A12.

3. The method of claim 1, where the plurality of biomarkers further comprises at least one of Alpha-2 Macroglobulin (A2M), Serum Amyloid A (SAA), and Apolipoprotein A1.

4. The method of claim 1, where the plurality of biomarkers comprises no more than 4 biomarkers.

5. The method of claim 1, where the step of determining the expression level of each biomarker comprises performing an assay selected from the group consisting of an enzyme-linked immunosorbent assay (ELISA), a radioimmunoassay (RIA), an immunofluorescent assay (IFA), a sandwich assay, a magnetic capture assay, a microsphere capture assay, a Western Blot assay, surface enhanced Raman spectroscopy (SERS), flow cytometry and mass spectrometry.

\* \* \* \* \*